(12) United States Patent
Krolik et al.

(10) Patent No.: US 8,939,991 B2
(45) Date of Patent: Jan. 27, 2015

(54) APPARATUS AND METHODS FOR REMOVING OBSTRUCTIVE MATERIAL FROM BODY LUMENS

(75) Inventors: Jeffrey A. Krolik, Campbell, CA (US); Daryush Mirzaee, Sunnyvale, CA (US); James H. Dreher, Santa Monica, CA (US); Juan Domingo, Lathrop, CA (US); Gwendolyn Watanabe, Sunnyvale, CA (US)

(73) Assignee: Hotspur Technologies, Inc., Mountain View, CA (US)

( * ) Notice: Subject to any disclaimer, the term of this patent is extended or adjusted under 35 U.S.C. 154(b) by 69 days.

(21) Appl. No.: 12/480,664

(22) Filed: Jun. 8, 2009

(65) Prior Publication Data

US 2010/0036312 A1 Feb. 11, 2010

Related U.S. Application Data

(60) Provisional application No. 61/078,330, filed on Jul. 3, 2008, provisional application No. 61/153,620, filed on Feb. 18, 2009, provisional application No. 61/059,796, filed on Jun. 8, 2008, provisional application No. 61/210,596, filed on Mar. 19, 2009.

(51) Int. Cl.
*A61B 17/221* (2006.01)
*A61B 17/32* (2006.01)
(Continued)

(52) U.S. Cl.
CPC .......... *A61B 17/221* (2013.01); *A61B 17/3207* (2013.01); *A61N 25/0068* (2013.01);
(Continued)

(58) Field of Classification Search
USPC ......... 606/127, 128, 159, 167, 169, 171, 180, 606/200, 113, 114, 166, 170; 604/22
See application file for complete search history.

(56) References Cited

U.S. PATENT DOCUMENTS

| 396,754 A | 1/1889 | Mayfield |
| 4,029,104 A | 6/1977 | Kerber |

(Continued)

FOREIGN PATENT DOCUMENTS

| CN | 1917802 A | 2/2007 |
| EP | 0 778 042 A2 | 6/1997 |

(Continued)

OTHER PUBLICATIONS

PCT International Search Report and Written Opinion for PCT/US2009/046659, Applicant: HotSpur Technologies, Inc., Forms PCT/ISA1220, PCT/ISA/210, and PCT/ISA/237; dated Jan. 27, 2010, 12 pages.

(Continued)

*Primary Examiner* — Kathleen Holwerda
(74) *Attorney, Agent, or Firm* — Baker & Hostetler LLP

(57) ABSTRACT

An apparatus is provided for removing material within a body lumen that includes a catheter including a proximal end, a distal end for introduction into a body lumen, and an aspiration lumen extending therebetween; a guide member extending from the distal end and terminating in a distal tip, the guide member comprising a track adjacent a track lumen extending from the distal tip into the aspiration lumen; and an obstruction clearing device deployable from the guide member and retractable along the track. In addition or alternatively, the apparatus includes a cutting head reciprocable within the aspiration lumen adjacent the distal end for macerating material being aspirated into the aspiration lumen.

15 Claims, 9 Drawing Sheets

(51) Int. Cl.
*A61B 17/3207* (2006.01)
*A61M 25/00* (2006.01)
*A61M 25/04* (2006.01)
*A61M 25/09* (2006.01)
*A61B 17/3205* (2006.01)
*A61B 17/22* (2006.01)
*A61M 25/10* (2013.01)

(52) U.S. Cl.
CPC .......... *A61M25/0082* (2013.01); *A61M 25/04* (2013.01); *A61M 25/09* (2013.01); *A61B 17/32056* (2013.01); *A61B 2017/22079* (2013.01); *A61B 2017/2217* (2013.01); *A61B 2017/320064* (2013.01); *A61B 2017/320775* (2013.01); *A61B 2217/005* (2013.01); *A61M 25/0074* (2013.01); *A61M 25/10* (2013.01); *A61M 2025/0096* (2013.01); *A61M 2025/09175* (2013.01); *A61M 2025/09183* (2013.01); *A61M 2025/1052* (2013.01)
USPC .......................... 606/127; 606/159; 606/171

(56) References Cited

U.S. PATENT DOCUMENTS

| | | | |
|---|---|---|---|
| 4,030,503 A | 6/1977 | Clark, III | |
| 4,273,128 A | 6/1981 | Lary | |
| 4,315,512 A | 2/1982 | Fogarty | |
| 4,545,367 A | 10/1985 | Tucci | |
| 4,646,742 A | 3/1987 | Packard et al. | |
| 4,649,922 A | 3/1987 | Wiktor | |
| 4,653,496 A * | 3/1987 | Bundy et al. | 606/159 |
| 4,706,671 A | 11/1987 | Weinrib | |
| 4,762,130 A | 8/1988 | Fogarty | |
| 4,784,636 A * | 11/1988 | Rydell | 604/22 |
| 4,813,934 A | 3/1989 | Engelson et al. | |
| 4,821,722 A | 4/1989 | Miller et al. | |
| 4,848,342 A | 7/1989 | Kaltenbach | |
| 4,848,344 A | 7/1989 | Sos et al. | |
| 4,890,611 A | 1/1990 | Monfort et al. | |
| 4,894,051 A * | 1/1990 | Shiber | 604/22 |
| 4,921,478 A | 5/1990 | Solano et al. | |
| 4,926,858 A * | 5/1990 | Gifford et al. | 606/159 |
| 4,950,277 A * | 8/1990 | Farr | 606/159 |
| 5,011,488 A | 4/1991 | Ginsburg | |
| 5,032,113 A | 7/1991 | Burns et al. | |
| 5,035,705 A | 7/1991 | Burns | |
| 5,059,176 A | 10/1991 | Winters | |
| 5,085,636 A | 2/1992 | Burns | |
| 5,090,959 A | 2/1992 | Samson et al. | |
| 5,100,388 A | 3/1992 | Behl et al. | |
| 5,100,423 A | 3/1992 | Fearnot | |
| 5,102,402 A | 4/1992 | Dror et al. | |
| 5,135,494 A | 8/1992 | Engelson et al. | |
| 5,135,531 A * | 8/1992 | Shiber | 606/159 |
| 5,141,518 A | 8/1992 | Hess et al. | |
| 5,171,221 A | 12/1992 | Samson | |
| 5,176,698 A | 1/1993 | Burns et al. | |
| 5,192,286 A | 3/1993 | Phan et al. | |
| 5,192,290 A | 3/1993 | Hilal | |
| 5,192,295 A | 3/1993 | Danforth et al. | |
| 5,207,229 A | 5/1993 | Winters | |
| 5,211,651 A | 5/1993 | Reger et al. | |
| 5,217,434 A | 6/1993 | Arney | |
| 5,221,260 A | 6/1993 | Burns et al. | |
| 5,259,839 A | 11/1993 | Burns | |
| 5,295,959 A | 3/1994 | Gurbel et al. | |
| 5,303,714 A | 4/1994 | Abele et al. | |
| 5,304,198 A | 4/1994 | Samson | |
| 5,308,356 A | 5/1994 | Blackshear et al. | |
| 5,312,340 A | 5/1994 | Keith | |
| 5,320,604 A | 6/1994 | Walker et al. | |
| 5,338,295 A | 8/1994 | Cornelius et al. | |
| 5,342,301 A | 8/1994 | Saab | |
| 5,364,354 A | 11/1994 | Walker et al. | |
| 5,368,567 A | 11/1994 | Lee | |
| 5,372,601 A | 12/1994 | Lary | |
| 5,378,238 A | 1/1995 | Peters et al. | |
| 5,380,282 A | 1/1995 | Burns | |
| 5,383,856 A | 1/1995 | Bersin | |
| 5,385,152 A | 1/1995 | Abele et al. | |
| 5,403,276 A * | 4/1995 | Schechter et al. | 604/22 |
| 5,415,634 A | 5/1995 | Glynn et al. | |
| 5,419,774 A * | 5/1995 | Willard et al. | 604/22 |
| 5,423,745 A * | 6/1995 | Todd et al. | 604/500 |
| 5,423,846 A | 6/1995 | Fischell | |
| 5,437,632 A | 8/1995 | Engelson | |
| 5,454,788 A | 10/1995 | Walker et al. | |
| 5,454,789 A | 10/1995 | Burns et al. | |
| 5,464,395 A | 11/1995 | Faxon et al. | |
| 5,476,477 A | 12/1995 | Burns | |
| 5,484,408 A | 1/1996 | Burns | |
| 5,484,409 A | 1/1996 | Atkinson et al. | |
| 5,484,411 A | 1/1996 | Inderbitzen et al. | |
| 5,487,730 A * | 1/1996 | Marcadis et al. | 604/103.07 |
| 5,527,326 A | 6/1996 | Hermann et al. | |
| 5,569,195 A | 10/1996 | Saab | |
| 5,569,201 A | 10/1996 | Burns | |
| 5,571,122 A | 11/1996 | Kelly et al. | |
| 5,624,396 A | 4/1997 | McNamara et al. | |
| 5,643,298 A | 7/1997 | Nordgren et al. | |
| 5,643,304 A * | 7/1997 | Schechter et al. | 606/171 |
| 5,658,302 A | 8/1997 | Wicherski et al. | |
| 5,662,603 A | 9/1997 | Gelbfish | |
| 5,665,098 A | 9/1997 | Kelly et al. | |
| 5,683,410 A | 11/1997 | Samson | |
| 5,693,015 A | 12/1997 | Walker et al. | |
| 5,728,067 A | 3/1998 | Enger | |
| 5,749,849 A | 5/1998 | Engelson | |
| 5,766,191 A | 6/1998 | Trerotola | |
| 5,776,099 A | 7/1998 | Tremulis | |
| 5,779,698 A | 7/1998 | Clayman et al. | |
| 5,807,328 A | 9/1998 | Briscoe | |
| 5,836,961 A | 11/1998 | Kieturakis et al. | |
| 5,843,103 A | 12/1998 | Wulfman | |
| 5,868,735 A | 2/1999 | Lafontaine | |
| 5,868,768 A | 2/1999 | Wicherski et al. | |
| 5,891,153 A * | 4/1999 | Peterson | 606/107 |
| 5,895,398 A | 4/1999 | Wensel et al. | |
| 5,906,606 A | 5/1999 | Chee et al. | |
| 5,919,162 A | 7/1999 | Burns | |
| 5,947,985 A | 9/1999 | Imran | |
| 5,954,737 A | 9/1999 | Lee | |
| 5,972,019 A | 10/1999 | Engelson et al. | |
| 5,980,486 A | 11/1999 | Enger | |
| 5,997,557 A * | 12/1999 | Barbut et al. | 606/159 |
| 6,004,328 A | 12/1999 | Solar | |
| 6,017,323 A | 1/2000 | Chee | |
| 6,036,717 A | 3/2000 | Mers et al. | |
| 6,050,972 A | 4/2000 | Azizi et al. | |
| 6,066,158 A | 5/2000 | Engelson et al. | |
| 6,090,126 A | 7/2000 | Burns | |
| 6,096,055 A | 8/2000 | Samson | |
| 6,113,579 A | 9/2000 | Eidenschink et al. | |
| 6,129,708 A | 10/2000 | Enger | |
| 6,146,396 A | 11/2000 | Konya et al. | |
| 6,210,370 B1 | 4/2001 | Chi-Sing et al. | |
| 6,231,543 B1 | 5/2001 | Hegde et al. | |
| 6,231,588 B1 | 5/2001 | Zadno-Azizi | |
| 6,245,040 B1 | 6/2001 | Inderbitzen et al. | |
| 6,283,950 B1 | 9/2001 | Appling | |
| 6,306,124 B1 | 10/2001 | Jones et al. | |
| 6,306,151 B1 | 10/2001 | Lary | |
| 6,325,778 B1 | 12/2001 | Zadno-Azizi et al. | |
| 6,350,252 B2 | 2/2002 | Ray et al. | |
| 6,440,097 B1 | 8/2002 | Kupiecki | |
| 6,454,775 B1 | 9/2002 | Demarais et al. | |
| 6,458,096 B1 | 10/2002 | Briscoe et al. | |
| 6,511,492 B1 | 1/2003 | Rosenbluth et al. | |
| 6,514,273 B1 | 2/2003 | Voss et al. | |
| 6,530,935 B2 | 3/2003 | Wensel et al. | |
| 6,542,781 B1 | 4/2003 | Koblish et al. | |
| 6,544,217 B1 | 4/2003 | Gulachenski | |

(56) References Cited

U.S. PATENT DOCUMENTS

| | | |
|---|---|---|
| 6,547,754 B1 | 4/2003 | Evans et al. |
| 6,558,401 B1 | 5/2003 | Azizi |
| 6,575,933 B1 | 6/2003 | Wittenberger et al. |
| 6,589,206 B1 | 7/2003 | Sharkawy et al. |
| 6,610,077 B1 | 8/2003 | Hancock et al. |
| 6,620,179 B2 | 9/2003 | Boock et al. |
| 6,626,861 B1 | 9/2003 | Hart et al. |
| 6,638,245 B2 | 10/2003 | Miller et al. |
| 6,660,014 B2 | 12/2003 | Demarais et al. |
| 6,666,874 B2 | 12/2003 | Heitzmann et al. |
| 6,679,860 B2 | 1/2004 | Stiger |
| 6,685,722 B1 | 2/2004 | Rosenbluth et al. |
| 6,711,444 B2 | 3/2004 | Koblish |
| 6,743,208 B1 | 6/2004 | Coyle |
| 6,824,545 B2 | 11/2004 | Sepetka et al. |
| 6,945,977 B2 | 9/2005 | Demarais et al. |
| 7,004,954 B1 | 2/2006 | Voss et al. |
| 7,058,456 B2 | 6/2006 | Pierce |
| 7,070,576 B2 | 7/2006 | O'Brien et al. |
| 7,087,039 B1 | 8/2006 | Cox et al. |
| 7,179,269 B2 | 2/2007 | Welch et al. |
| 7,182,755 B2 | 2/2007 | Tal |
| 7,186,237 B2 | 3/2007 | Meyer et al. |
| 7,244,270 B2 | 7/2007 | Lesh |
| 7,250,042 B2 | 7/2007 | Kataishi et al. |
| 7,306,617 B2 | 12/2007 | Majercak |
| 7,338,501 B2 | 3/2008 | Teague et al. |
| 7,377,931 B2 | 5/2008 | Bagaoisan |
| 7,462,183 B2 | 12/2008 | Behl et al. |
| 7,507,246 B2 | 3/2009 | McGuckin et al. |
| 7,517,352 B2 | 4/2009 | Evans et al. |
| 7,758,604 B2 | 7/2010 | Wu et al. |
| 7,819,887 B2 | 10/2010 | McGuckin et al. |
| 7,862,576 B2 | 1/2011 | Gurm |
| 7,873,404 B1 | 1/2011 | Patton |
| 7,879,066 B2 | 2/2011 | Desai et al. |
| 7,883,516 B2 | 2/2011 | Huang et al. |
| 8,043,313 B2 | 10/2011 | Krolik et al. |
| 2001/0031981 A1 | 10/2001 | Evans et al. |
| 2002/0010487 A1 | 1/2002 | Evans et al. |
| 2002/0133117 A1 | 9/2002 | Azizi et al. |
| 2002/0177870 A1 | 11/2002 | Sepetka et al. |
| 2003/0004542 A1 | 1/2003 | Wensel et al. |
| 2003/0009190 A1 | 1/2003 | Kletschka et al. |
| 2003/0163158 A1 | 8/2003 | White |
| 2004/0006361 A1 | 1/2004 | Boyle et al. |
| 2004/0133232 A1 | 7/2004 | Rosenbluth et al. |
| 2004/0181150 A1 | 9/2004 | Evans et al. |
| 2004/0236363 A1 | 11/2004 | Kieturakis et al. |
| 2004/0243156 A1 | 12/2004 | Wu et al. |
| 2004/0243167 A1 | 12/2004 | Tanaka et al. |
| 2005/0038383 A1 | 2/2005 | Kelley et al. |
| 2005/0059993 A1 | 3/2005 | Ramzipoor et al. |
| 2005/0131453 A1 | 6/2005 | Parodi |
| 2005/0288632 A1 | 12/2005 | Willard |
| 2006/0009784 A1 | 1/2006 | Behl et al. |
| 2006/0036277 A1 | 2/2006 | Kieturakis et al. |
| 2006/0074442 A1 | 4/2006 | Noriega et al. |
| 2006/0106407 A1 | 5/2006 | McGuckin et al. |
| 2006/0200047 A1 | 9/2006 | Galdonik et al. |
| 2006/0253145 A1 | 11/2006 | Lucas |
| 2007/0016244 A1 | 1/2007 | Behl et al. |
| 2007/0038225 A1 | 2/2007 | Osborne |
| 2007/0083158 A1 | 4/2007 | Hirszowicz et al. |
| 2007/0129752 A1 | 6/2007 | Webler et al. |
| 2007/0239182 A1 | 10/2007 | Glines et al. |
| 2007/0293935 A1 | 12/2007 | Olsen et al. |
| 2008/0064930 A1 | 3/2008 | Turliue |
| 2008/0117257 A1 | 5/2008 | Sagara et al. |
| 2008/0125798 A1 | 5/2008 | Osborne et al. |
| 2008/0177277 A1 | 7/2008 | Huang et al. |
| 2008/0200873 A1 | 8/2008 | Espinosa et al. |
| 2008/0228209 A1 | 9/2008 | DeMello et al. |
| 2008/0262487 A1 | 10/2008 | Wensel et al. |
| 2008/0269798 A1 | 10/2008 | Ramzipoor et al. |
| 2008/0306440 A1 | 12/2008 | Hirszowicz et al. |
| 2009/0018549 A1 | 1/2009 | Desai et al. |
| 2009/0018569 A1 | 1/2009 | Desai et al. |
| 2009/0076539 A1 | 3/2009 | Valaie |
| 2010/0036410 A1 | 2/2010 | Krolik et al. |
| 2010/0137892 A1 | 6/2010 | Krolik et al. |
| 2011/0093000 A1 | 4/2011 | Ogle et al. |
| 2011/0125132 A1 | 5/2011 | Krolik et al. |
| 2012/0078096 A1 | 3/2012 | Krolik et al. |
| 2012/0109057 A1 | 5/2012 | Krolik et al. |
| 2012/0197193 A1 | 8/2012 | Krolik et al. |

FOREIGN PATENT DOCUMENTS

| | | |
|---|---|---|
| JP | S62-233168 A | 10/1987 |
| JP | S63-192457 A | 8/1988 |
| JP | H03-080872 A | 4/1991 |
| JP | H08-509397 A | 10/1996 |
| JP | 2004-136103 A | 5/2004 |
| JP | 2008-504067 A | 2/2008 |
| WO | WO-94/18894 A1 | 9/1994 |
| WO | 2008117256 A3 | 10/2008 |
| WO | 2008117257 A3 | 10/2008 |
| WO | WO-2011/011765 A2 | 1/2011 |

OTHER PUBLICATIONS

Supplementary European Search Report dated Oct. 9, 2013.
Communication Pursuant to Article 94(3) EPC mailed Jun. 18, 2014, as received in European Patent Application No. 09774584.8.
Examination Report mailed Jun. 23, 2014, as received in Singaporean Patent Application No. 2010090801.
Extended European Search Report mailed Oct. 17, 2013, as received in European Patent Application No. 09774584.8.
First Office Action mailed Jul. 16, 2013, as received in Chinese Patent Application No. 201080040808.2, and an English language summary thereof.
First Office Action mailed Jul. 23, 2013, as received in Japanese Patent Application No. 2011-512752, and an English language summary thereof.
First Office Action mailed Jun. 3, 2014, as received in Japanese Patent Application No. 2012-521865.
First Office Action mailed Nov. 1, 2012, as receiving in Chinese Patent Application No. 200980129911.1, and an English language translation thereof.
International Search Report and Written Opinion mailed Apr. 11, 2011, as received in International Application No. PCT/US2010/043165.
International Search Report and Written Opinion mailed Dec. 6, 2012, as received in International Application No. PCT/US2012/025734.
International Search Report and Written Opinion mailed Feb. 1, 2010, as received in International Application No. PCT/US2009/049639.
International Search Report and Written Opinion mailed Mar. 18, 2013, as received in International Application No. PCT/US2012/061672.
Invitation to Respond to Written Opinion mailed Nov. 8, 2012, as received in Singaporean Patent Application No. 2010090801.
Notice of Rejection mailed Mar. 4, 2014, as received in Japanese Patent Application No. 2011-512752, and an English language summary thereof.
Notice of Rejection mailed Sep. 3, 2013, as received in Japanese Patent Application No. 2011-516896, and an English language summary thereof.
Office Action mailed Sep. 13, 2012, as received in Chinese Patent Application No. 200980134164.0.
Patent Examination Report No. 1 mailed Mar. 13, 2013, as received in Australian Patent Application No. 2009266808.
Second Office Action mailed Mar. 19, 2013, as received in Chinese Patent Application No. 201080040808.2, and an English language summary thereof.

* cited by examiner

US 8,939,991 B2

APPARATUS AND METHODS FOR REMOVING OBSTRUCTIVE MATERIAL FROM BODY LUMENS

RELATED APPLICATIONS

This application claims benefit of U.S. provisional application Ser. Nos. 61/059,796, filed Jun. 8, 2008, 61/078,330, filed Jul. 3, 2008, 61/153,620, filed Feb. 18, 2009, and 61/210,596, filed Mar. 19, 2009, the entire disclosures of which are expressly incorporated by reference herein.

FIELD OF THE INVENTION

The present invention relates generally to apparatus for removing material within a body lumen of a patient. More particularly, the present invention relates to apparatus for removing or otherwise capturing thrombus or other obstructive material from within a tubular graft, blood vessel, or other body lumen, e.g., by cutting, separating, and/or aspiration of material, and to methods for making and using such apparatus.

BACKGROUND

Flow within a blood vessel or other body lumen within a patient's vasculature may become constricted or ultimately interrupted for a variety of reasons. For example, a vessel may gradually narrow due to inflammation and/or cell proliferation. In addition, thrombus may form due to such narrowing or other flow problems within a vessel.

For example, an aorto-venous graft may be implanted in an arm of a patient experiencing kidney failure, e.g., to facilitate dialysis treatment. Such grafts may be a fistula formed directly in the patient's body, e.g., through tissue between an adjacent artery and vein or other vessels, may be a xenograft implanted between two vessels, or may be a synthetic graft. Such grafts only have a limited life cycle due to inflammation, thrombus formation, and the like. Once such a graft becomes sufficiently occluded or otherwise deteriorates, a new graft must be implanted at a new location for subsequent treatment.

Some medical procedures involve aspirating material from within a body lumen. Although it may be desirable to provide a relatively large aspiration lumen in a catheter or other device to facilitate aspiration, many procedures require the device to maintain a relatively small profile, e.g., to provide desired tracking performance and/or avoid damaging the passages through which the device is directed. In such devices, relatively large particles may obstruct the aspiration lumen of the device, preventing further aspiration.

Accordingly, apparatus and methods for removing material from aorto-venous grafts, blood vessels, or other body lumens would be useful.

SUMMARY

The present invention is directed to apparatus for removing material within a body lumen of a patient. More particularly, the present invention is directed to apparatus for removing or otherwise capturing thrombus or other obstructive material within a tubular graft, blood vessel, or other body lumen, e.g., by cutting, separating, and/or aspiration the material, and to methods for making and using such apparatus.

In accordance with a first embodiment, an apparatus is provided for removing material within a body lumen that includes an elongate tubular member including a proximal end, a distal end sized for introduction into a body lumen, and an aspiration lumen extending between the proximal and distal ends; a guide member extending from the distal end and terminating in a distal tip, the guide member comprising a track adjacent a track lumen extending from the distal tip into the aspiration lumen; and an obstruction clearing device deployable from the guide member and retractable along the track.

In an exemplary embodiment, the obstruction clearing member includes a core wire slidable within the track lumen and one or more lumen clearing elements deployable from the distal tip of the guide member when the core wire is advanced relative to the guide member. The lumen clearing element(s) may include an expandable structure that is expanded from a contracted condition within the guide member to an expanded condition when deployed from the guide member, e.g., for engaging material within a body lumen. The expandable structure may be directable proximally along the track in the expanded condition, e.g., when the core wire is subsequently retracted relative to the guide member, for drawing the lumen clearing element(s) and any captured material into the aspiration lumen of the tubular member.

In addition, the guide member may include an orifice, e.g., in a side wall thereof, communicating with the track lumen, the orifice located within the aspiration lumen such that, when the core wire is retracted relative to the guide member, the expandable structure is compressed inwardly towards the contracted condition and the lumen clearing element(s) are drawn through the orifice into the track lumen. For example, the lumen clearing element(s) may be oriented substantially axially within the track lumen when the one or more lumen clearing elements are drawn through the orifice into the track lumen. When the core wire is subsequently advanced relative to the guide member, the lumen clearing element(s) may be directed through the track lumen in the contracted condition until the lumen clearing element(s) are redeployed from the distal tip of the guide member.

In accordance with another embodiment, a method is provided for removing material within a body lumen of a patient. A distal end of a tubular member may be introduced into a body lumen, the tubular member having a guide member extending distally from the distal end. The tubular member may be positioned such that the distal end is disposed adjacent material to be removed and a distal tip of the guide member is disposed beyond the material. One or more lumen clearing elements may be deployed from the distal tip of the guide member, each lumen clearing element including an expandable structure that expands from a contracted condition within the guide member to an expanded condition when deployed from the distal tip. The deployed lumen clearing element(s) may be retracted along a track of the guide member to engage material within the body lumen and draw the material into a lumen of the tubular member.

When the lumen clearing element(s) are retracted along the track of the guide member, the lumen clearing element(s) may be retracted through an orifice into the guide member to compress and/or draw the expandable structure(s) into the guide member. If desired, the lumen clearing element(s) may be redeployed from the distal tip of the guide member after retracting the one or more lumen clearing elements through the orifice into the guide member. This process may be repeated as often as desired to remove material from the body lumen.

Optionally, the material may be aspirated before or while being drawn into the lumen of the tubular member, e.g., to facilitate removing the material from the body lumen. In addition or alternatively, the material engaged by the lumen clearing elements may be separated by the expandable structure into multiple pieces, e.g., as the expandable structure is directed into the tubular member lumen and/or compressed back towards the contracted condition.

In accordance with still another embodiment, an apparatus is provided for removing material within a body lumen that includes an elongate tubular member including a proximal end, a distal end sized for introduction into a body lumen, and an aspiration lumen extending between the proximal and distal ends; and a cutting head disposed within the aspiration lumen adjacent the distal end. The cutting head is reciprocable axially or otherwise movable within the aspiration lumen for breaking up material being aspirated into the aspiration lumen.

In accordance with yet another embodiment, a method is provided for removing material within a body lumen of a patient. A distal end of a tubular member may be introduced into a body lumen, the tubular member including an aspiration lumen and a cutting head disposed within the aspiration lumen near the distal end. The tubular member may be positioned such that the distal end is disposed adjacent material to be removed and/or vacuum pressure may be applied to the aspiration lumen to draw material within the body lumen towards the distal end of the tubular member. The cutting head may be activated, e.g., before, after, or when the vacuum pressure is applied, to cause the cutting head to reciprocate relative to the distal end to macerate material drawn to the distal end of the tubular member. The cutting head may break the material into pieces sufficiently small to be aspirated into the aspiration lumen by the vacuum pressure.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

DETAILED DESCRIPTION OF THE EXEMPLARY EMBODIMENTS

Figure 1:
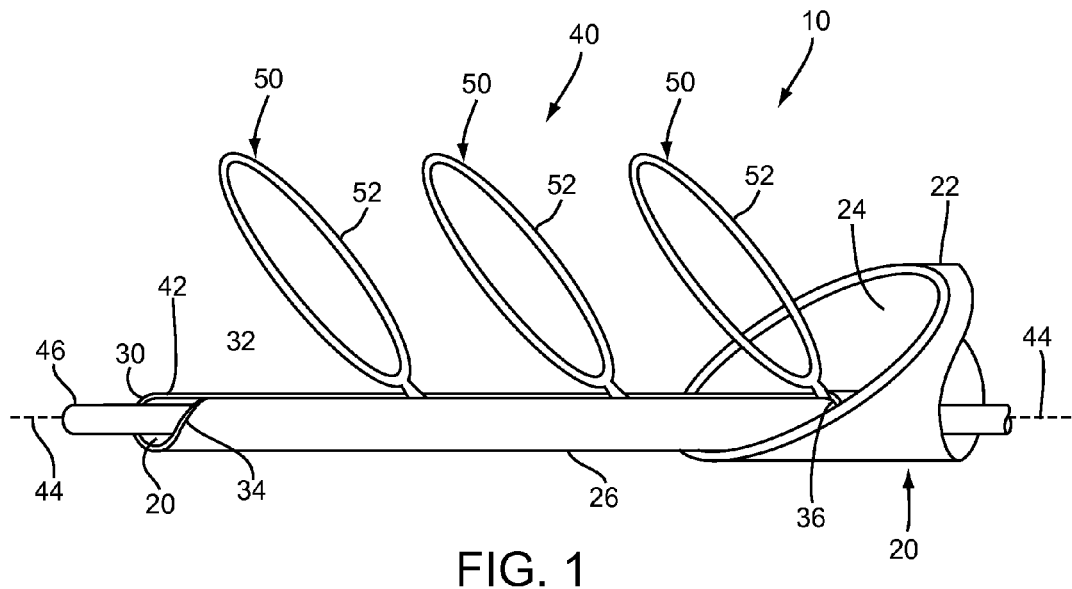
FIG. 1 is a side view of a distal end of an exemplary embodiment of an apparatus for capturing material within a body lumen, the apparatus including a plurality of lumen clearing elements deployable along a track of a catheter.
Figure 2:
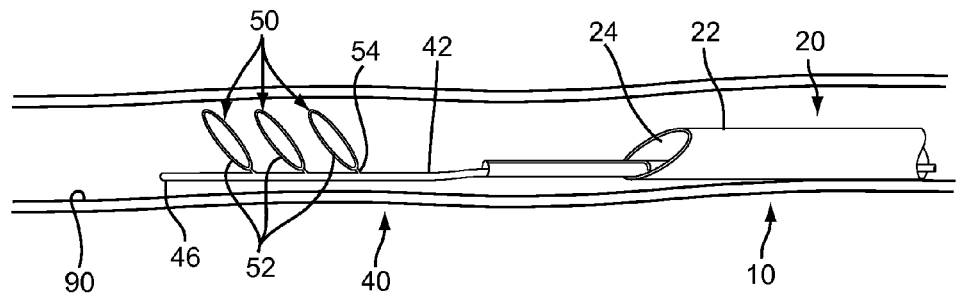
FIG. 2 is a cross-sectional view of a body lumen, showing the apparatus of FIG. 1 positioned therein with the lumen clearing elements deployed from the track within the body lumen.

Turning to the drawings, FIGS. 1 and 2 show an exemplary embodiment of an apparatus 10 for removing, retrieving, and/or otherwise capturing thrombus, objects, and/or obstructive material from within a body lumen 90, such as a blood vessel, aorto-venous fistula, tubular graft, and the like. Generally, the apparatus 10 includes a catheter, sheath, or other tubular member 20, and an obstruction clearing or retrieval device 40 including one or more lumen clearing appendages or elements 50 carried by a core wire, shaft, or other elongate member 42.

In the embodiment shown, the catheter 20 includes a proximal end (not shown), a distal end 22, and a lumen 24 extending therebetween. In addition, the catheter 20 includes a guide member 26 extending distally from the distal end 22, e.g., attached to or integrally formed with the distal end 24 of the catheter 20. Alternatively, the guide member 26 may be movable relative to the catheter 20, e.g., to allow the guide member 26 to be advanced from and/or retracted into the lumen 24 of the catheter 20 during use.

The guide member 26 includes a track lumen 28 that extends at least partially from within the catheter 20, e.g., from within the lumen 24 to a distal tip 30 of the guide member 26. The guide member 26 may terminate within the distal end 22 of the catheter 20, e.g., at a predetermined length therein corresponding to the length of the lumen clearing element(s) 50 and/or the region of the shaft 42 carrying the lumen clearing element(s) 50. Alternatively, the guide member 26 may extend substantially to the proximal end of the catheter 20 (not shown).

The guide member 26 may allow the lumen clearing element(s) 50 to be deployed from and/or drawn into the guide member 26 during use, as described further below. For example, the guide member 26 may include a track or other feature for guiding the lumen clearing element(s) 50 along the guide member. In the embodiment show, the guide member 26 includes a slit 32 that extends from the catheter 20, e.g., from within or adjacent the distal end 22, to the distal tip 30 of the guide member 26. The slit 32 may be oriented inwardly towards the lumen 24 of the catheter 20, e.g., to guide the lumen clearing element(s) 50 into the lumen 24 of the catheter, as described further below.

The distal tip 30 of the guide member 26 may be substantially atraumatic, e.g., rounded or otherwise shaped to reduce risk of damaging walls of body lumens within which the apparatus 10 is introduced. In addition, the distal tip 30 may include a tapered entrance 34 communicating with the slit 32, e.g., to guide the lumen clearing element(s) 50 into the slit 32, as described further below. The guide member 26 also includes an orifice 36, e.g., at an end of the slit 32 opposite the tapered entrance 34, e.g., within the lumen 24 of the catheter 20. The orifice 36 may be sized and/or shaped to allow the lumen clearing element(s) 50 to be drawn into the track lumen 28 of the guide member 26, e.g., as described further below.

Optionally, the catheter 20 may include one or more additional lumens (not shown) extending between the proximal end and the distal end 22, e.g., for delivering and/or aspirating fluid, for receiving a guidewire or other rail (not shown), and the like. For example, in some applications, it may be desirable to advance the entire apparatus 10 over a guidewire or other rail (not shown), e.g., by loading the guidewire through a guidewire lumen (also not shown) disposed adjacent the lumen 24, or through the lumen 24 itself. In addition, or alternatively, a source of fluid, e.g., one or more solvents or other therapeutic agents, a source of vacuum, e.g., a syringe, a vacuum line, and the like, may be coupled to the catheter 20, e.g., for delivering or aspirating material through the lumen 24 or other lumen (not shown) in the catheter 20.

For example, the apparatus 10 may include a handle (not shown) coupled to or otherwise on the proximal end of the catheter 20, e.g., for manipulating the catheter 20 and/or the entire apparatus 10. The handle may include one or more controls or actuators (also not shown) for actuating the obstruction clearing device 40 and/or other components of the apparatus 10. In addition, the handle may include one or more ports (not shown) for coupling to a source of fluid and/or vacuum. For example, one of the ports may communicate with the lumen 24 and a vacuum line, syringe, or other source of vacuum may be coupled to the port to allow aspiration of material within or adjacent the lumen 24, e.g., as described further below. Exemplary embodiments of handles that may be provided on the apparatus 10 are disclosed in provisional application Ser. No. 61/078,330, filed Jul. 3, 2008, the entire disclosure of which is expressly incorporated by reference herein.

With continued reference to FIGS. 1 and 2, the core wire 42 of the obstruction clearing device 40 generally includes a proximal end, e.g., within the proximal end of the catheter 20 (not shown), and a distal end terminating in a distal tip 46, e.g., defining a longitudinal axis 44 for the apparatus 10. The core wire 42 may be a substantially flexible elongate member, e.g., a solid or hollow wire structure, having sufficient length to extend from the proximal end of the catheter 20 through and beyond the guide member 26.

For example, the core wire 42 may have sufficient length to extend from a target site within a patient's body through the catheter 20 to a location outside the patient's body. Alternatively, the core wire 42 may extend to and be coupled to other components of the apparatus 10 spaced apart proximally from the lumen clearing element(s) 50. The core wire 42 may have sufficient column strength to allow advancement of the core wire 42 through the catheter 20 without substantial risk of buckling or kinking. For example, a distal region of the core wire 42 may be relatively flexible and a proximal region may be substantially rigid or semi-rigid to facilitate advancement of the distal region from the proximal end of the catheter 20. The core wire 42 may be formed from a single wire strand, multiple strands, a coiled wire structure, and the like having a sufficiently small profile to be slidably received in the catheter 20 and/or guide member 26.

In an exemplary embodiment, the proximal end of the core wire 42 may be received within and/or otherwise coupled to a handle (not shown). The handle may be mounted or otherwise provided on the proximal end of the catheter 20, as described above, and may include an actuator, e.g., a slider control, button, and the like (not shown) for directing the core wire 42 axially relative to the catheter 20, e.g., to deploy and/or retract the lumen clearing element(s) 50 from the guide member 26, as explained further below.

The distal tip 46 of the core wire 42 may be substantially atraumatic, e.g., rounded or otherwise shaped to minimize risk of perforation and/or catching during advancement from the guide member 26 within a patient's body. Optionally, the distal tip 46 may be covered by a coiled wire and/or a polymeric covering, and/or may include a "J" or other curved tip (not shown).

With particular reference to FIG. 1, as shown, the obstruction clearing device 40 includes a plurality of the lumen clearing elements 50 for capturing material within a body lumen. Although three lumen clearing elements 50 are shown, it will be appreciated that the apparatus may include fewer or more elements, e.g., only one or two, or four or more, as desired. Each lumen clearing element 50 may include an expandable structure that may be compressed to allow advancement through the track lumen 28 of the guide member 26 and expanded to extend at least partially across a body lumen.

In the exemplary embodiment shown in FIGS. 1 and 2, each lumen clearing element 50 includes an enclosed hoop 52 coupled to an arm 54 extending from the core wire 42. Each respective hoop 52 and arm 54 may be integrally formed together, for example, by forming the hoop 52 and arm 54 from a flat sheet, e.g., by laser cutting, die cutting, stamping, and the like, by bending or otherwise forming a wire into the hoop shape with one end of the wire providing the arm 54 and the other end attached to the arm 52 to enclose the hoop 52, and the like. Each arm 54 may be attached at predetermined locations on the core wire 42, e.g., spaced apart from one another by a desired spacing, e.g., by bonding, welding, soldering, and the like. For example, one end of each arm 54 by attached to a side of the core wire 42 such that the arms 54 are aligned axially with one another. The arms 54 may be spaced apart by a distance such that the hoops 52 do not substantially overlap one another when compressed to the contracted condition, e.g., to reduce an overall profile of the lumen clearing elements 50 when compressed into the track lumen 28 of the guide member 26.

One of each arm 54 may be attached directly to the core wire 42. Alternatively, a portion of each arm 54 may be wrapped at least partially around the core wire 54 and/or each arm 54 may be attached to a collar or sleeve (not shown) that may be attached to the core wire 54 such that the arms 54 are spaced apart and axially aligned with one another.

In an exemplary embodiment, the hoops 52 and/or arms 54 may be formed from elastic or superelastic material. Thus, the hoops 52 may be compressed radially inwardly to a contracted condition (not shown) sufficiently small to be directed into and along the track lumen 28 of the guide member 26, yet resiliently expandable towards an expanded, relaxed condition, as shown, in which the hoops 52 extend transversely from the core wire 42. Exemplary materials for the lumen clearing element(s) 50 include metals, such as Nitinol or stainless steel, polymers or other plastics, or composite materials. The hoops 52 and/or arms 54 may be heat treated or otherwise set to biased to the expanded condition yet resiliently compressible to the contracted condition.

In the relaxed condition, the hoops 52 may have a circular or elliptical shape, e.g., approximating a desired range of diameters of body lumens to be treated using the apparatus 10. For example, the hoops 52 may have a size sufficient to extend substantially across a body lumen 90 in the expanded condition, e.g., having a diameter or minor elliptical axis between about two and ten millimeters (2-10 mm) and/or a circumference or other perimeter length between about six and thirty millimeters (6-30 mm). In the relaxed condition, the arms 54 may be biased to extend transversely relative to the core wire 42 and longitudinal axis 44 at a desired angle, e.g., between about thirty and ninety degrees (30-90°). As shown, in the relaxed condition, the arms 54 and hoops 52 may extend away from the distal end 22 of the catheter 20, although, alternatively, they may extend substantially perpendicular to or towards the distal end 22, if desired.

The arms 54 may have a length relatively smaller than the size of the hoops 52, e.g., between about half to two millimeters (0.5-2.0 mm). Thus, the arms 54 may simply provide flexible hinges to allow the hoops 52 to be deployed from and retracted into the track lumen 28 of the guide member 26.

In the contracted condition, each hoop 52 may be compressible inwardly, e.g., such that side regions of the hoops 52 between the arm 52 and the outer region opposite the arm 52 are directed towards one another. Thus, in the contracted condition, the hoops 52 may have a cross-section smaller than the diameter of the track lumen 28 of the guide member 26, e.g., between about half to two millimeters (0.5-2.0 mm), as described further below. Also in the contracted condition, the arms 54 may be bendable inwardly towards the core wire 42, e.g., such that the hoops 52 extend substantially parallel to the longitudinal axis 44 to facilitate the hoops 52 being received in and directed along the track lumen 28 of the guide member 26, as described further below.

The hoops 52 may have a variety of cross-sections or thicknesses, e.g., a circular cross-section, which may provide a substantially atraumatic shape to prevent damaging the wall of a body lumen within which the element(s) 50 are deployed. Alternatively, other cross-sections may be provided along the entire perimeter of the hoops 52 or only at desired regions, e.g., between the side and outer regions, to provide one or more cutting edges, e.g., to facilitate removing adherent material from the wall of a body lumen within which the element(s) 50 are deployed. For example, a single cutting edge may be provided on each of the hoops 52 or multiple cutting edges, e.g., extending along an outer or leading edge of the hoops 52 or spirally around the hoops 52, as desired. In addition or alternatively, the thickness of the hoops 52 may be varied around their perimeter to provide a variable flexibility to different regions of the hoops 52, if desired.

Figure 4:
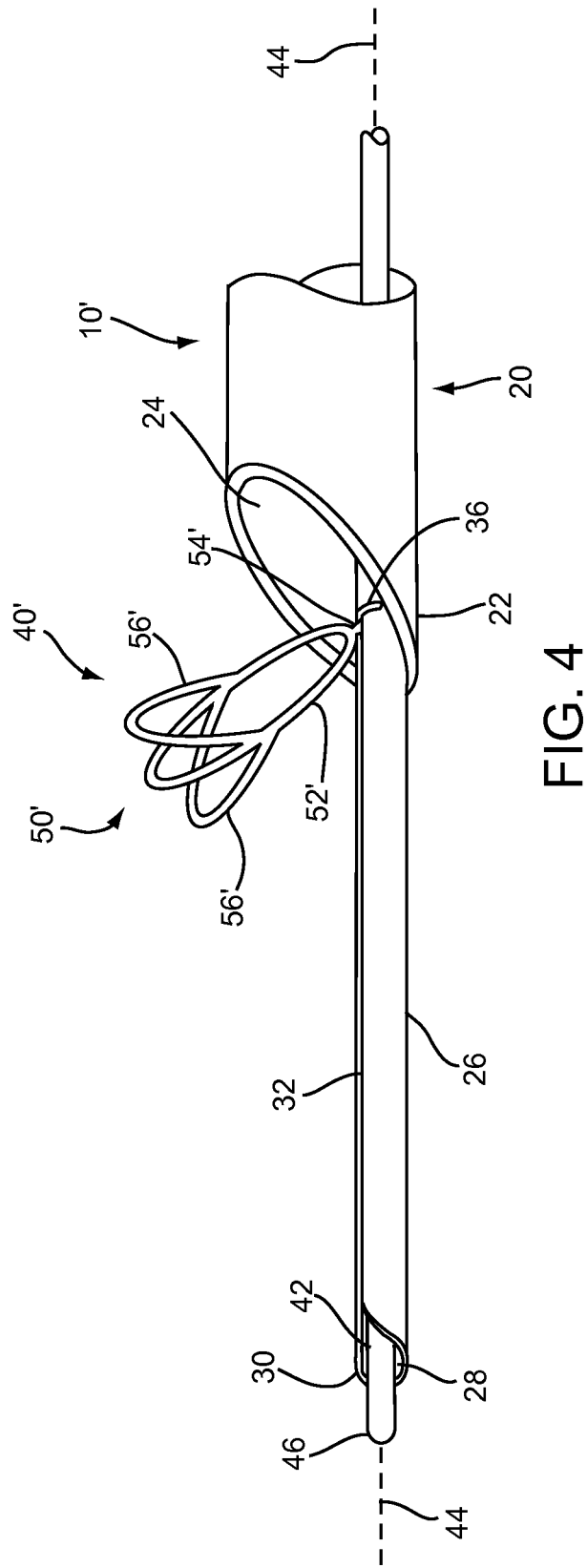
FIG. 4 is a side view of a distal end of another exemplary embodiment of an apparatus for capturing material from within a body lumen that includes an alternate configuration for a lumen clearing element.

Optionally, if desired, the lumen clearing element(s) may include one or more additional features, e.g., to facilitate capturing material therein and/or removing adherent material from a wall of a body lumen being treated. For example, FIG. 4 shows an alternative embodiment of an lumen clearing element 50' that includes a hoop 52' coupled to an arm 54' extending from a core wire 42, similar to the previous embodiment. However, unlike the previous embodiment, additional loops 56' are provided on the hoop 52,' e.g., that extend from side regions of the hoop 52.' The loops 56' may be substantially symmetrical relative to the outer region of the hoop 52,' e.g., with one loop 56' on either side of the outer region of the hoop 52,' as shown. Thus, in this embodiment, the lumen clearing element 50' splits into three separate loops around a midpoint of the hoops 52,' which may reduce spacing between the loops. This embodiment may facilitate breaking up thrombus or other material as it is contacted by the lumen clearing element(s) 50' and/or drawn into the catheter 20, e.g., as described further below.

Figure 3A:
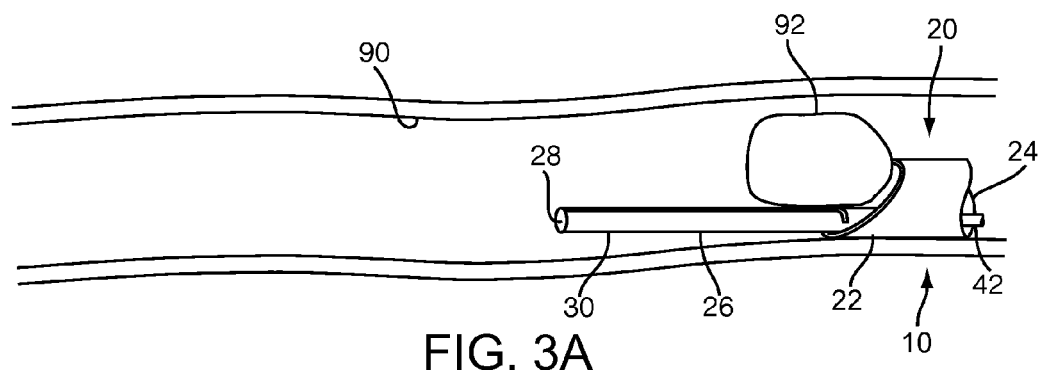
FIGS. 3A-3G are cross-sectional views of a body lumen showing a method for capturing material from the body lumen using the apparatus of FIGS. 1 and 2.
Figure 3B:
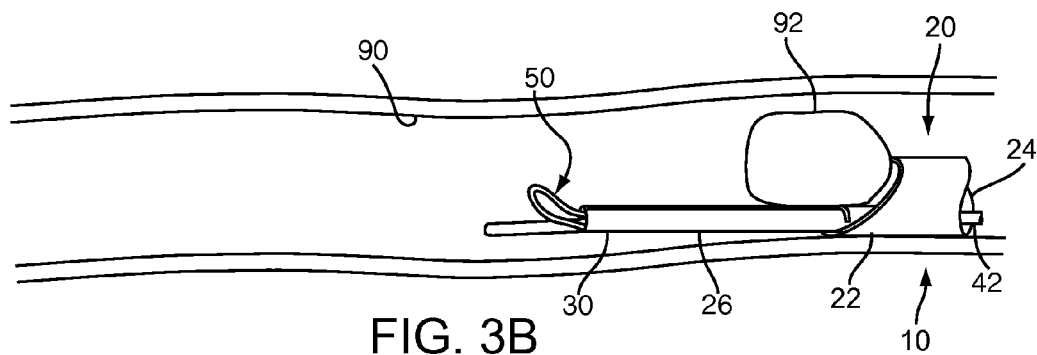

During manufacturing assembly or during preparation immediately before use, the apparatus 10 is provided with the obstruction clearing device 40 loaded into the catheter 20, e.g., such that the lumen clearing elements 50 are compressed into the contracted condition within the track lumen 28 of the guide member 26 (not shown, see generally FIGS. 3A-3B).

For example, during manufacturing, the guide member 26 may be attached to the catheter 20 such that the guide member 26 extends from the proximal end of the catheter 20 beyond the distal end 22 of the catheter 20, as described above. Alternatively, the guide member 26 may extend only a short distance into the distal end 22 of the catheter 20. The catheter 20 may include a co-extrusion or other tubular body that includes both the lumen 24 and a guide lumen (not shown), and the guide member 26 may be coupled to the catheter 20 such that the track lumen 28 of the guide member 26 communicates with the guide lumen. The catheter 20 and/or guide member 26 may be constructed as a single tubular component along their length or may be formed from multiple tubular components attached together, e.g., to provide a desired rigidity and/or flexibility at difference regions along the length of the catheter 20 and/or guide member 26. For example, the proximal regions may be relatively rigid or semi-rigid to facilitate advancement of the catheter 20 and/or guide member 26, while the distal regions may be relatively flexible to facilitate advancement through tortuous anatomy.

To make the obstruction clearing device 40, the lumen clearing elements 50 may be formed and attached to the core wire 42, e.g., as described above. The core wire 42 may be backloaded into the lumen 28 of the guide member 26, e.g., until a proximal end of the core wire 42 extends towards or to the proximal end of the catheter 20. The proximal end of the core wire 42 may be coupled to an actuator, e.g., on a handle on the proximal end of the catheter 20. The core wire 42 may be directed proximally, e.g., using the actuator on the handle or before coupling to the actuator, to draw the lumen clearing elements 50 into the lumen 28 of the guide member 26, thereby compressing the lumen clearing elements 50 into the contracted condition, similar to the method described below for retracting the lumen clearing elements 50 during use.

Optionally, if desired, the apparatus 10 may include one or more markers to facilitate positioning and/or advancement of the apparatus 10 during use. For example, one or more radiopaque markers may be placed on the obstruction clearing device 40, e.g., on the core wire 42, hoops 52, and/or arms 54. Alternatively, the lumen clearing elements 50 or components thereof may be formed from radiopaque or other materials that may facilitate imaging the apparatus 10 during use. For example, radiopaque markers and/or materials may facilitate positioning or otherwise imaging the apparatus 10 using fluoroscopy or other x-ray imaging, e.g., when deploying and/or actuating the basket device 40. Alternatively, echogenic markers and/or materials may be provided to facilitate imaging using ultrasound or similar imaging techniques.

Turning to FIGS. 3A-3G, an exemplary method is shown for retrieving, removing, or otherwise capturing material 92 within a body lumen 90, e.g., using an apparatus 10, which may be any of the embodiments described herein, and not necessarily limited to the embodiment shown and described below with reference to FIGS. 1 and 2. The body lumen 90 may be a blood vessel, e.g., a vein or artery, a graft, e.g., an aorto-venous fistula, tubular xenograft, or synthetic tubular graft, and the like. For example, the body lumen 90 may be a passage communicating between an adjacent artery and vein (not shown), e.g., in an arm or other region of a dialysis patient. Alternatively, the body lumen 90 may be a blood vessel within a patient's vasculature, e.g., a peripheral vessel in a patient's leg, a cerebral vessel, and the like. In a further alternative, the material 92 may be a stone within a patient's urinary tract or other foreign object to be removed from the patient's body.

Optionally, the body lumen 90 may be accessed using one or more additional instruments (not shown), which may be part of a system or kit including the apparatus 10. For example, an introducer sheath, guide catheter, or other tubular member (not shown) may be introduced adjacent the target site where the material is to be removed, or may be introduced elsewhere in the patient's body to provide access to the patient's vasculature or other passages communicating with the body lumen 90. If the body lumen 90 is located in a peripheral vessel of the patient, a percutaneous puncture or cut-down may be created using a needle or other instrument (not shown) at a peripheral location (also not shown), such as a femoral artery, carotid artery, or other entry site, and an introducer sheath may be placed through the puncture at the peripheral location to provide access. The apparatus 10 may be advanced through the patient's vasculature from the entry site, e.g., alone or with the aid of a guide catheter, guidewire, and the like (not shown).

For example, to facilitate directing the apparatus 10 from an entry site to the target body lumen 90, a guide catheter, micro-catheter, or other tubular body may be placed from the entry site to the body lumen 90 using conventional methods. In addition or alternatively, a guidewire (not shown) may be placed from the entry site to the body lumen 90 if desired, e.g., if the apparatus 10 includes a guidewire lumen in the catheter 20 or core wire 42.

Initially, as shown in FIG. 3A, the apparatus 10 has been advanced into the body lumen 90 such that the guide member 26 extends through or otherwise beyond the material 90 being captured. Optionally, one or more fluids may be delivered into the body lumen 90, e.g., to facilitate imaging and/or positioning the apparatus 10. For example, radiopaque fluid may be delivered into the body lumen 90 via the lumen 24 of the catheter 20 (or via a lumen in the core wire 42 or the track lumen 28 of the guide member 26) to facilitate locating and/or measuring the size of the material 92 using fluoroscopy. Markers (not shown) on the apparatus 10 may facilitate positioning the guide member 26 and/or distal end of the catheter 20 relative to the material 92 before the obstruction clearing device 40 is deployed, e.g., to facilitate verifying that the distal tip 30 of the guide member 26 is positioned distal to the material 92.

Optionally, at this point or any time hereafter, a source of vacuum communicating with the lumen 24 of the catheter 20 may be activated to aspirate the material 92 or segments thereof and/or fluid into the lumen 24. In addition or alternatively, the vacuum may be applied to maintain the material 92 adjacent the distal end 22 of the catheter 20, e.g., to prevent migration of the material 92 during subsequent steps of the procedure.

Figure 3C:
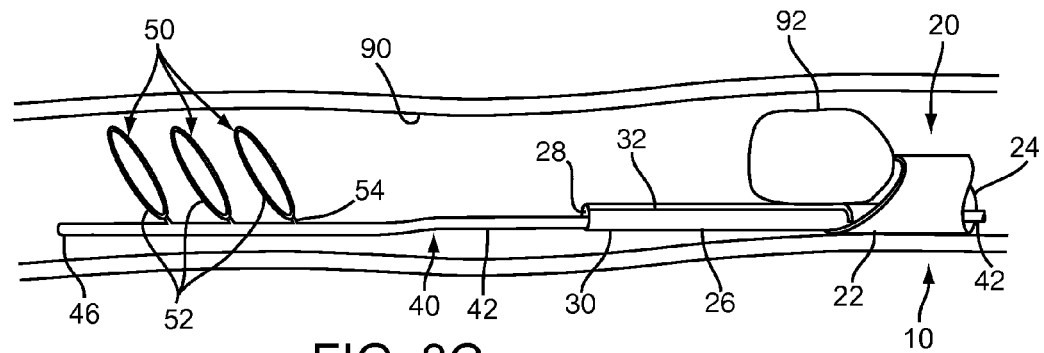

Turning to FIG. 3B, the obstruction clearing device 40 may then be deployed within the body lumen 90, e.g., such that the lumen clearing elements 50 are disposed distally beyond the material 92. As shown, the core wire 42 may emerge first from the track lumen 28 beyond the distal tip 30 of the guide member 26, and then the lumen clearing elements 50 may become exposed, whereupon the lumen clearing elements 50 may resiliently and automatically expand to the expanded condition within the body lumen 90, as shown in FIG. 3C. Because the distal tip 30 of the guide member 26 is positioned distally beyond the material 92, the lumen clearing elements 50 are deployed well beyond the material 92, which may reduce the risk of deploying the lumen clearing elements 50 within or adjacent the material 92 and dislodging the material 92 or segments prematurely.

Figure 3D:
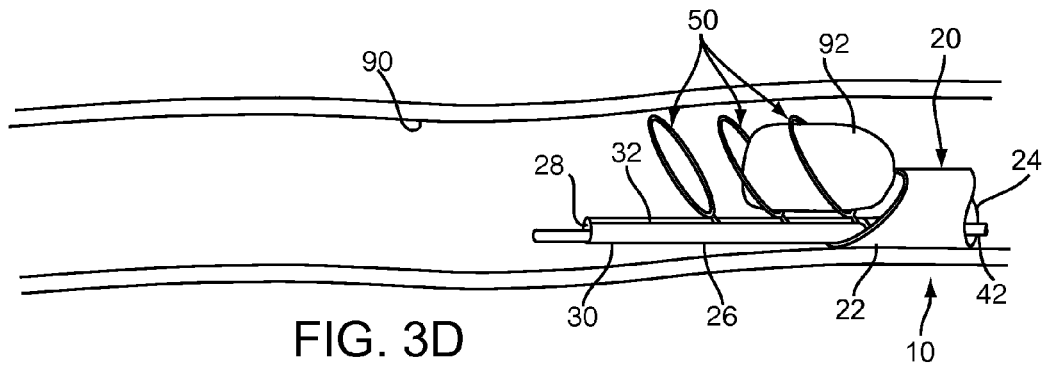

With further reference to FIG. 3D, the obstruction clearing device 40 may then be retracted relative to the catheter 20 and guide member 26. As shown, as the core wire 42 is withdrawn back into the track lumen 28 of the guide member 26, the arms 54 of each successive lumen clearing element 50 may contact the distal tip 30 and be guided by the tapered entrance 34 into the slit 32. The slot 32 may be sufficiently wide that the arms 54 pass freely into and along the slot 32 with the hoops 52 remaining deployed substantially in the expanded condition, as shown. Thus, the hoops 52 may substantially surround, engage, and/or otherwise capture the material 92 within one or more of the hoops 52, e.g., depending on the length and/or size of the material 92.

Figure 3E:
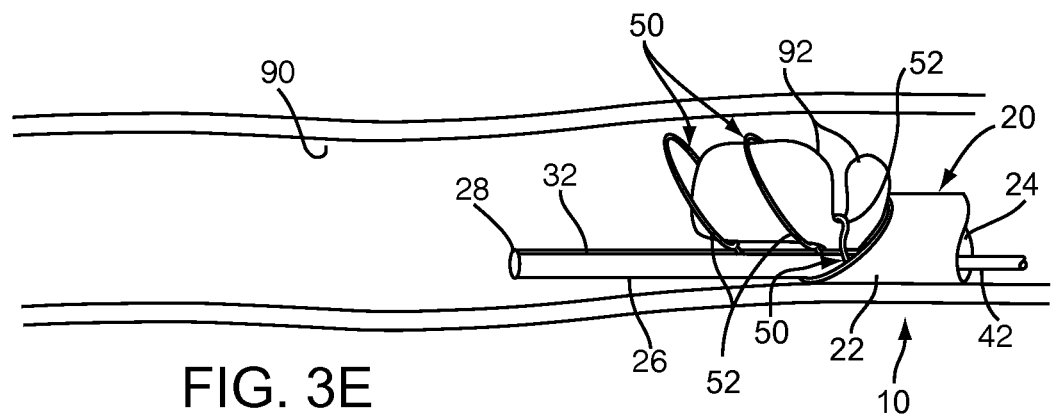

As shown in FIG. 3E, as the obstruction clearing device 40 is retracted further, the hoops 52 of the lumen clearing elements 50 are pulled through the distal end 22 of the catheter 20 into the lumen 24. As the outer region of the hoops 52 enter the lumen 24, the material 92 may be cut or otherwise separated if it is too large to be drawn into the lumen 24 in a single piece. The smaller pieces may be drawn into the lumen 24 due to aspiration provided by the vacuum within the lumen 24 and/or pulled in by the hoop 52 entering the distal end 22. If remaining pieces of the material 92 are too large to be drawn into the lumen 22, they may remain immediately outside the distal end 22, e.g., due to the aspiration pressure, until the next hoop 52 engages and/or cuts the material 92 further. Thus, multiple successive lumen clearing elements 50 may facilitate breaking the material 92 into pieces sufficiently small to be drawn into the lumen 24 by aspiration.

If desired, the material 92 may be treated, e.g., at least partially dissolved, macerated, and the like before, during, or after withdrawal of the lumen clearing elements 50 into the catheter 20. For example, a therapeutic agent may be delivered into the body lumen 90 via the catheter 20 (e.g., through lumen 24 or another infusion lumen, not shown), e.g., to at least partially dissolve or separate thrombus or other relatively soft material before being drawn into the lumen 24 of the catheter 20.

Optionally, the hoops 52 of the lumen clearing elements 50 may include one or more cutting edges (not shown), which may facilitate separating the material 92 into multiple pieces. In addition or alternatively, such cutting edge(s) may facilitate scraping a wall of the body lumen 90, e.g., to remove adherent material from the wall of the body lumen 90 and facilitate capturing the material.

Figure 3F:
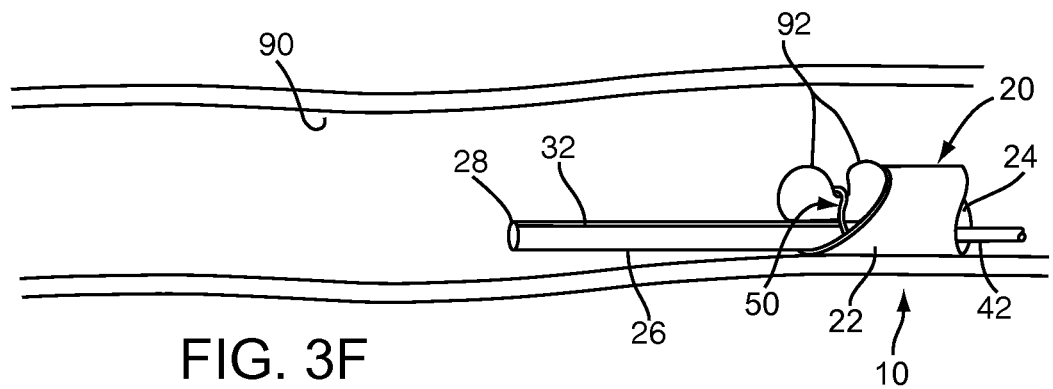
Figure 3G:
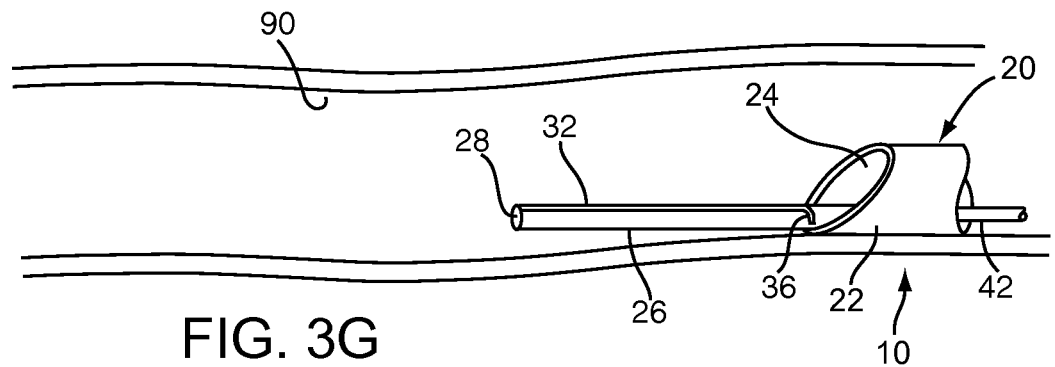

As shown in FIG. 3F, the final lumen clearing element 50 has been drawn into the lumen 24, along with the captured material 92. As the lumen clearing elements 50 enter the lumen 24, the hoops 52 may be compressed inwardly towards the contracted condition and/or the arms 54 may be bent to accommodate receiving the hoops 52 within the lumen 24. As can be seen in FIG. 3G (and FIG. 1), the slit 32 in the guide member 26 communicates with the orifice 36 within the distal end 22 of the catheter 20. The orifice 36 may be sufficiently large, e.g., wide to receive the hoops 52 therethrough, thereby allowing the hoops 52 to be drawn through the orifice 36 into the track lumen 28. As this occurs, the lumen clearing elements 50 may be compressed into the contracted condition, e.g., oriented substantially axially within the track lumen 28 of the guide member 26.

In this orientation, if desired, the obstruction clearing device 40 may be advanced distally again to direct the lumen clearing elements 50 distally through the track lumen 28 of the guide member 26, e.g., until the lumen clearing elements 50 are deployed from the distal tip of the guide member 26, as shown in FIGS. 3B and 3C. Thus, the steps shown in FIGS. 3B-3G may be repeated as many times as desired, e.g., to capture additional pieces of material 92 within the body lumen 90. Optionally, the catheter 20 may be repositioned within the body lumen 90, e.g., advanced distally further into the body lumen 90 to capture additional material (not shown) therein.

Because the lumen clearing elements may be retracted and redeployed as often as desired, the obstruction clearing device may include any number of lumen clearing elements. For example, as shown in FIG. 4, the obstruction clearing device 40' includes only one lumen clearing element 50, which may be deployed and then retracted repeatedly to break up and/or capture material within a body lumen. The material may be easily broken into pieces small enough to be drawn into the lumen 24 of the catheter 20 by aspiration or otherwise. Once all of the desired material has been removed, the apparatus 10 (e.g., with the lumen clearing element(s) withdrawn into the guide member 26) may be withdrawn from the body lumen and/or the patient's body.

The process may be repeated, as desired, using the same apparatus 10 or a different apparatus (not shown). For example, the obstruction clearing device 40 may be withdrawn into the catheter 20 and then directed to another location within the body lumen 90 or other elsewhere in the patient's body, and then redeployed to capture additional material, and the process may be repeated as often as desired.

Figure 5:
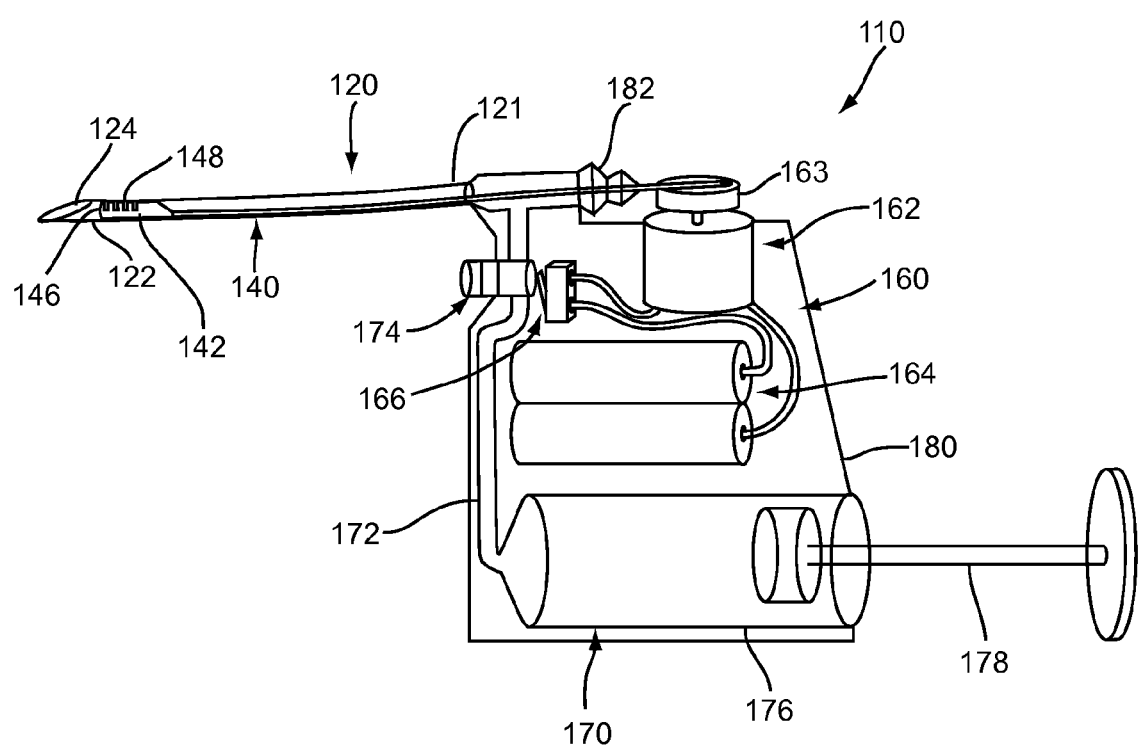
FIG. 5 is a side of an exemplary embodiment of another apparatus for capturing material within a body lumen that includes a reciprocating cutting head deployable from a catheter.

Turning to FIG. 5, another embodiment of an apparatus 110 is shown for removing material from a body lumen. Generally, the apparatus 110 includes a catheter, sheath, or other tubular member 120 and a cutting assembly 140 disposed within the catheter 110. In addition, the apparatus 110 includes a control system 160, e.g., for moving the cutting element 140 relative to the catheter 120, and a vacuum source 170, which may be disposed within a handle 180 of the apparatus 110. Optionally, the apparatus 110 may include a guide member and obstruction clearing device (not shown), if desired, which may be used in combination with the cutting assembly 140, e.g., with the obstruction clearing device drawing material into the catheter 120 and the cutting assembly 140 breaking the material up to facilitate aspiration, as described further below.

The catheter generally 120 includes a proximal end 121, a distal end 122 sized for introduction into a body lumen, and one or more lumens, e.g., an aspiration lumen 124, extending between the proximal and distal ends 121, 122. Optionally, the catheter 120 may include one or more additional lumens (not shown), e.g., a guidewire lumen, a shaft lumen, and the like, if desired. The catheter 120 may be constructed similar to the previous embodiments, e.g., having a desired length and/or flexibility for accessing a body lumen within a patient's body to be treated. The relative size of the catheter 120 and handle 180 shown in FIG. 5 are not to scale, but are merely intended to illustrate the various components of the apparatus 110. In particular, the handle 180 has been shown substantially larger than its actual size relative to the catheter 120 to facilitate identification of the components within the handle 180.

The cutting assembly 140 generally includes a cutting head 142 disposed adjacent the distal end 122 of the catheter 120 and a drive shaft 144 extending proximally from the cutting head 142, e.g., to the proximal end 121 of the catheter 120, as shown. The cutting head 142 terminates in a rounded tip 146 and includes one or more teeth 148, e.g., along a side edge of the cutting head 142. The cutting head 142 has a width smaller than the diameter of the aspiration lumen 124, e.g., slightly smaller than the aspiration lumen 124 such that the cutting head 142 is free to move axially within the aspiration lumen 124 with minimal lateral movement. Alternatively, the cutting head 142 may have a width substantially smaller than the aspiration lumen 124 and may be movable along one side of the catheter wall, e.g., with the teeth 148 oriented inwardly towards the center of the aspiration lumen 124.

Figure 7A:
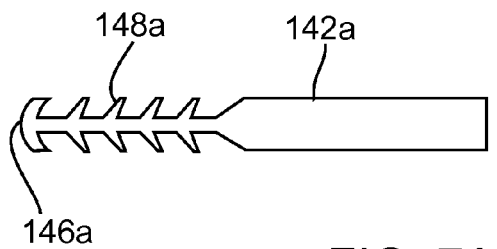
FIGS. 7A-7D are side views of alternative embodiments of cutting heads that may be included in the apparatus of FIG. 5.
Figure 7B:
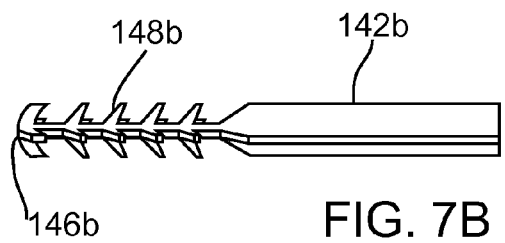
Figure 7C:
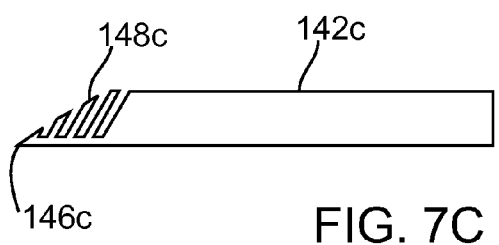
Figure 7D:
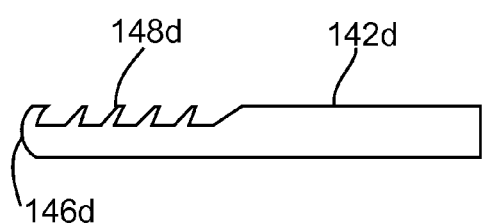
Figure 8A:
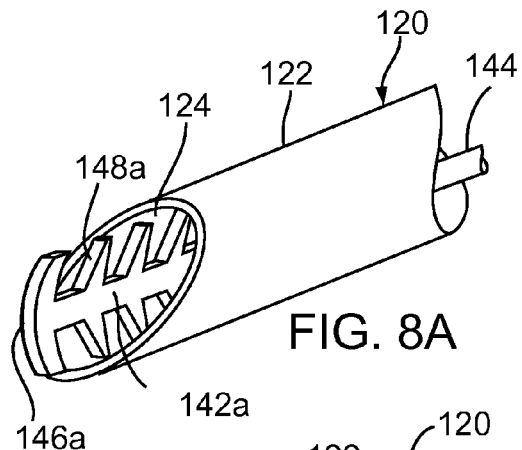
FIGS. 8A-8D are perspective details of the cutting heads of FIGS. 7A-7D, respectively, being deployed from a distal end of a catheter.
Figure 8B:
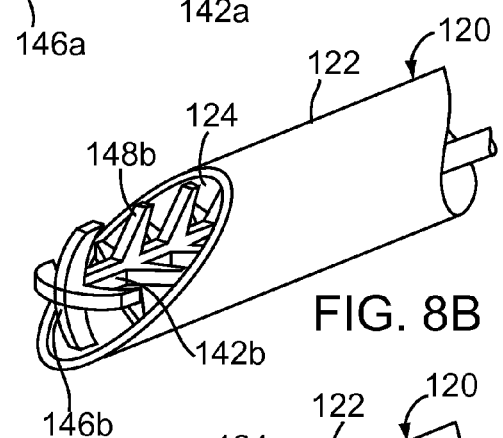
Figure 8C:
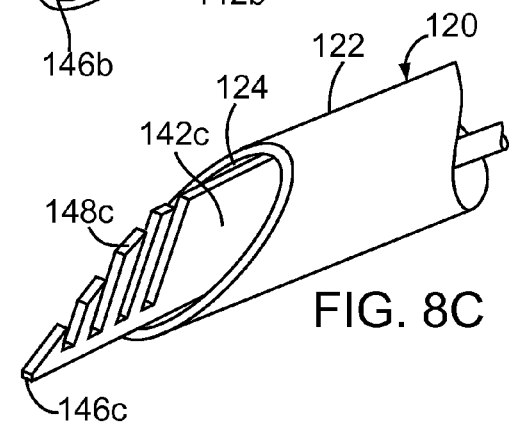
Figure 8D:
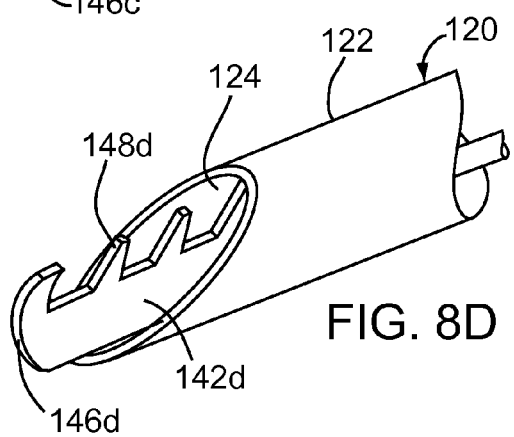

FIGS. 7A-7D are side views of alternative embodiments of cutting heads 142 that may be provided for the cutting assembly 140 of FIG. 5. For example, the cutting head 142a of FIG. 7A includes a rounded tip 146a and a plurality of teeth 148a along opposite side edges of the cutting head 142a. FIG. 7B shows a similar cutting head 142b that includes four sets of teeth 148b spaced apart ninety degrees from one another, each set of teeth 148b extending axially along a cutting length of the cutting head 142b. The cutting head 142c of FIG. 7C terminates in a sharpened tip 146c and includes a set of teeth 148c tapering to the tip 146c. FIG. 7D shows a cutting head 142d that includes a rounded tip 146d and one set of teeth 148d, similar to that shown in FIG. 5, except that the teeth 148d are angled diagonally, e.g., proximally away from the tip 146d. Such angled teeth 148d may facilitate cutting, tearing, breaking up, or otherwise macerating material engaged by the teeth 148d and pulling the material into the aspiration lumen 124, as described further below. Similar to the cutting head 142 of FIG. 5, the cutting heads 142a-142d may be movable within the aspiration lumen 124 of a catheter 120, as shown in FIGS. 8A-8D, respectively, and described further below.

Returning to FIG. 5, the cutting head 142 (or any of the alternatives shown in FIGS. 7A-7D) may be formed from a substantially rigid sheet, bar, or other base material, e.g., by machining, laser cutting, stamping, casting, molding, and the like, thereby providing the desired shape for the tip 146 and teeth 148. The cutting head 142 may be integrally formed with the shaft 144 or may be attached to the shaft 144 subsequent to forming the cutting head 142, e.g., by welding, soldering, bonding, mating connectors (not shown), and the like. The shaft 144 may be formed from a substantially rigid or semi-rigid solid or hollow wire, rod, or other material, e.g., having sufficient column strength to allow the cutting head 142 to be reciprocated or otherwise moved from the proximal end 121 of the catheter 120. The cutting head 142 and/or shaft 144 may be formed from a variety of materials, e.g., metals, such as stainless steel, plastic, or composite materials.

The shaft 144 may have a relatively small diameter or other cross-section compared to the cutting head 144, e.g., such that the shaft 144 occupies minimal space within the aspiration lumen 124 of the catheter 120. Thus, material aspirated into the aspiration lumen 124 of the catheter 120 may be free to pass along the aspiration lumen 124 with minimal resistance caused by the shaft 144. Alternatively, the shaft 144 may enter and travel along a separate shaft lumen (not shown) in the catheter 120, e.g., extending from a location adjacent the distal end 122 to the proximal end 121, e.g., if it is desired to separate the shaft 144 substantially from material traveling through the aspiration lumen 124.

Returning to FIG. 5, the proximal end 121 of the catheter 120 may be coupled to the handle 180 such that the shaft 144 extends into the handle 180, e.g., through one or more seals 182. In exemplary embodiments, the seal(s) 182 may include a piston/cylinder arrangement, a bellows, and the like. The shaft 144 may be coupled to the control system 160, e.g., such that the shaft 144 may be reciprocated or otherwise moved relative to the catheter 120. For example, the control system 160 may include a motor for driving the shaft 144, e.g., by coupling the shaft 144 to an output 163 of the motor 162. The control system 160 may also include a power source 164, e.g., a battery pack, rechargeable battery, a cable for connecting to an electrical outlet (not shown), and the like, coupled to the motor 162 and an electrical switch 166 for selectively supplying power from the power source 164 to the motor 162 for turning the motor 162 off and on.

The vacuum source 170 is coupled to the aspiration lumen 124 of the catheter 120, e.g., via line 172 that communicates with the aspiration lumen 124. In the exemplary embodiment shown, the vacuum source 170 may be a syringe 176 including a plunger 178, which may be drawn to create a vacuum within the syringe 176 and then locked in position to maintain the vacuum. Alternatively, the vacuum source may be an external vacuum source, e.g., house vacuum in a facility, an external pump, and the like.

A fluid valve 174 is provided in the line 172 that may be actuated by a user to selectively open and close the line 172, e.g., to supply a vacuum pressure to the aspiration lumen 124 from the syringe 176. The fluid valve 174 may be coupled to the switch 166 such that, when a user activates the fluid valve 174 to aspirate the aspiration lumen 124, the switch 166 turns on the motor 162, causing the cutting head 142 to reciprocate. Alternatively, there may be a delay between opening the fluid valve 174 and turning on the motor 162 or the motor 162 may be turned on independently of the vacuum source 160. When the fluid valve 174 is deactivated to close the line 172, the switch 166 turns the motor 162 off, or the motor 162 may be turned off independently, either before or after turning off the vacuum source 160.

Figure 6A:
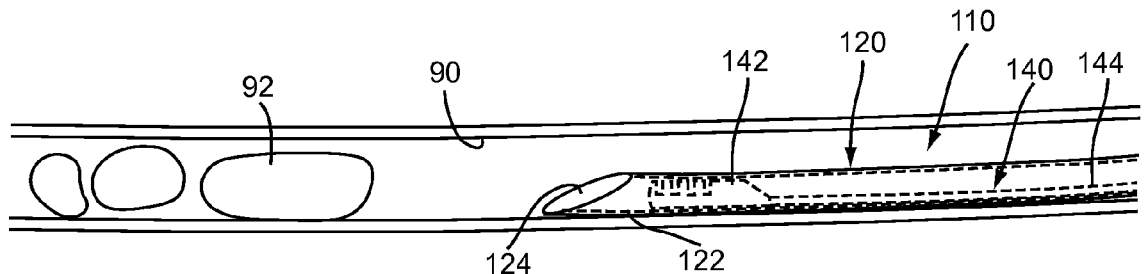
FIGS. 6A-6D are cross-sectional views of a body lumen showing a method for capturing material within the body lumen using the apparatus of FIG. 5.
Figure 6B:
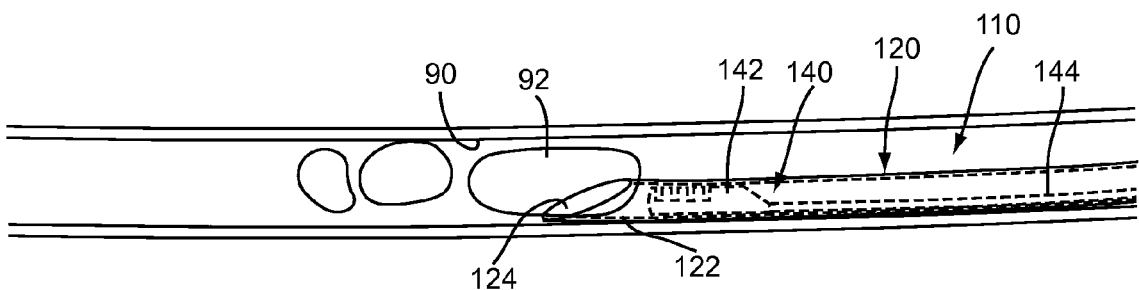

Turning to FIGS. 6A-6D, an exemplary method is shown for using the apparatus 110 of FIG. 5 to remove material 92 from a body lumen 90. The body lumen 90 may be a tubular graft, blood vessel, or other location within a patient's body accessed similar to the previous embodiments described above. As shown in FIG. 6A, the distal end 122 of the catheter 120 is positioned within the body lumen 90, e.g., from a percutaneous or other entry site, with the cutting assembly 140 and aspiration deactivated. Turning to FIG. 6B, a vacuum may be applied to the aspiration lumen 124, thereby drawing the material 92 within the lumen 90 towards the distal end 122 of the catheter 120. For example, as described above with additional reference to FIG. 5, the plunger 178 may be drawn to create a vacuum within syringe 176 and then locked or otherwise secured to maintain the vacuum within the syringe 176. Alternatively, an external source of vacuum (not shown) may be coupled to the handle 180 to apply a vacuum to the line 172. The fluid valve 174 may be opened to apply the vacuum to the aspiration lumen 124 of the catheter 120.

Figure 6C:
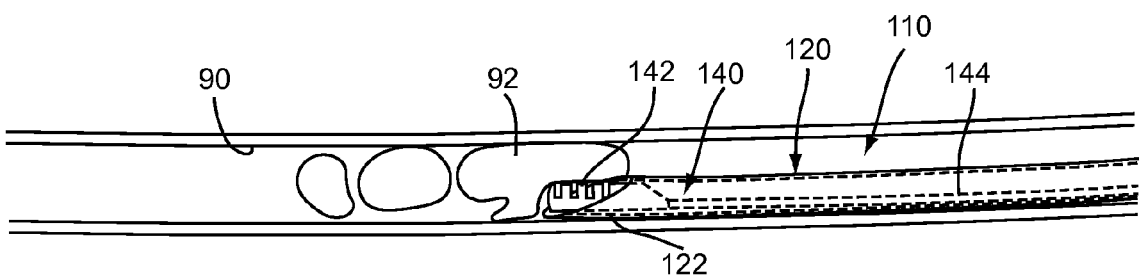

As shown, the material 92 may be too large to be drawn into the aspiration lumen 124 despite the vacuum. Turning to FIG. 6C, however, when the fluid valve 172 is opened, the switch 166 is substantially simultaneously activated to turn on the motor 162 and begin reciprocation of the cutting head 142. Alternatively, the switch 166 may be activated independently of the fluid valve 172, e.g., before or after opening the fluid valve 172. Once the motor 162 is activated, the cutting head 142 may reciprocate from a proximal or first position within the distal end 122 of the catheter 120 (shown in FIGS. 5 and 6B) to a distal or second position extending at least partially from the distal end 122 (shown in FIG. 6C).

Figure 6D:
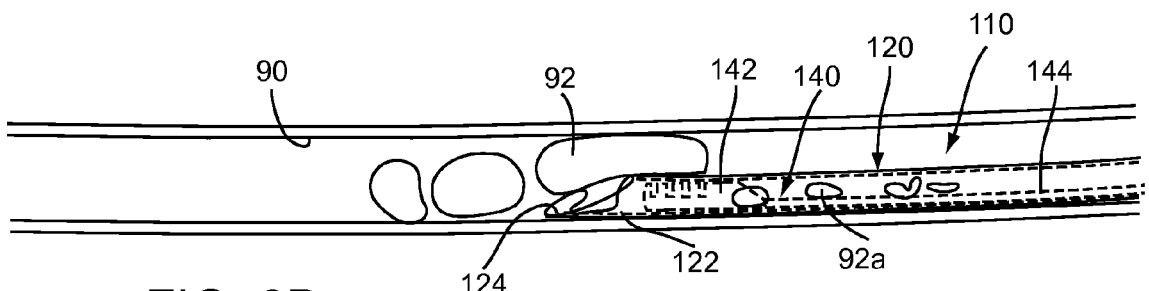

When the cutting head 142 moves to the distal position, the tip 146 of the cutting head 142 may initially contact the material 92, e.g., to begin breaking the material 92 up into smaller particles or pieces. The teeth 148 may also contact the material 92, e.g., to push the material upwardly and/or pull the material 92 proximally, which may cut, break, or otherwise separate the material 92 into smaller pieces 92a. As shown in FIG. 6D, the smaller pieces 92a may be sufficiently small to pass freely into the aspiration lumen 124 due to the vacuum being applied, thereby removing the pieces 92a from the body lumen 90 into the catheter 110, e.g., into the syringe 176 or other storage chamber (not shown) in the handle 180. It may take several reciprocations to fully macerate and aspirate the material 92 within the body lumen 90. The proximal oriented teeth, such as the teeth 148a-148d shown in FIGS. 7A-7D, may facilitate tearing off pieces 92a of the material 92, e.g., when the cutting head 142a-142d is withdrawn back into the distal end 122 of the catheter 120.

The motor 162 and consequently the cutting head 142 may be operated at speeds sufficiently fast to minimize the chance of the material 92 deforming and moving out of the way of the teeth 148 during reciprocation. For example, it may be desirable to operate the cutting head 142 at speeds of about 3,600-60,000 cycles per minute, e.g., about ten thousand cycles per minute or more. Such speeds may substantially prevent the material 92 from moving out of the way of the cutting head 142, which may result in a more complete and quick maceration and aspiration of the material 92.

Figure 9:
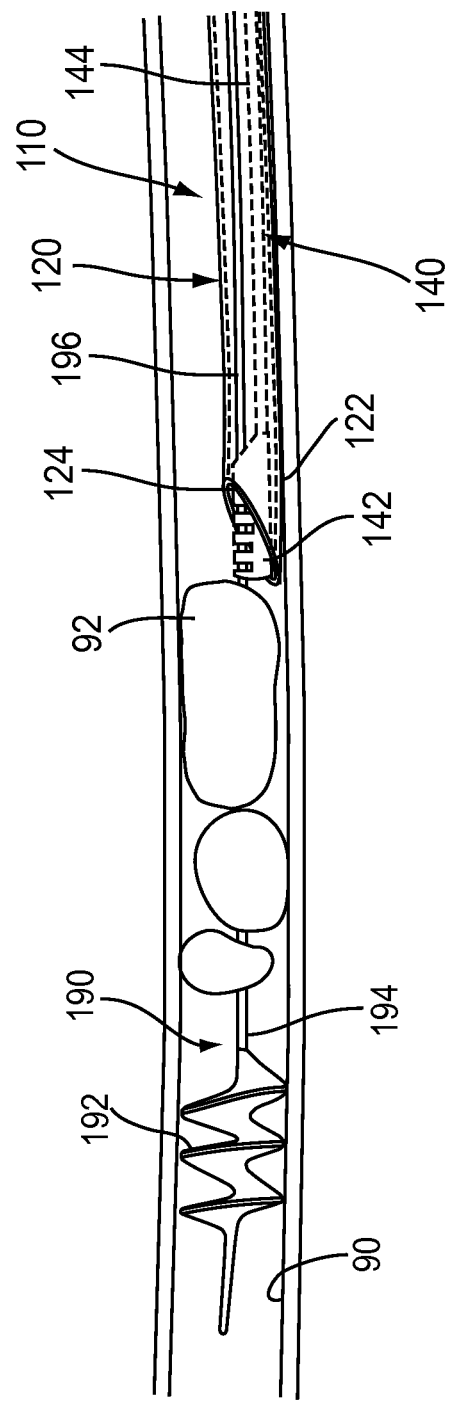
FIG. 9 is a cross-sectional view of a body lumen showing an exemplary embodiment of a system for capturing material from the body lumen that includes the apparatus of FIG. 5 and an expandable device for directing material within the body lumen towards the apparatus.

Turning to FIG. 9, in an alternative embodiment, the apparatus 110 of FIG. 5 may be used in cooperation with an expandable flow restoration device 190, e.g., to provide a system for removing material 92 from a body lumen 90. The flow restoration device 190 may include an expandable member 192 on a distal end 194 of a shaft 196, e.g., a catheter, sheath, or other tubular body. The expandable member 192 may be a balloon, a mechanically expandable structure, and the like. In the embodiment shown, the expandable member 192 may be a helical device, such as those disclosed in co-pending provisional application Ser. No. 61/153,620, filed Feb. 18, 2009, the entire disclosure of which is expressly incorporated by reference herein.

The shaft 196 of the flow restoration device 190 may be slidably received within a lumen of the catheter 120, e.g., the aspiration lumen 124 or another lumen provided within the catheter 120. In one embodiment, the distal end 194 of the flow restoration device 190 (with the expandable member 192 collapsed, not shown) may be inserted into a port in the proximal end of the catheter 120 and advanced through the catheter 120 after the catheter 120 has been positioned in the body lumen 90. The distal end 194 of the flow restoration device 190 may be advanced completely through the material 92 obstructing the body lumen 90, whereupon the expandable member 192 may be expanded, as shown.

Alternatively, a guidewire or other rail (not shown) may be placed in the body lumen 90 before the apparatus 110 and/or flow restoration device 190. The flow restoration device 190 may be advanced over the guidewire into the body lumen 90 and positioned as desired. The catheter 120 may then be advanced over the shaft 196 of the flow restoration device 190 or over a separate guidewire (not shown), e.g., until the catheter 120 is positioned relative to the flow restoration device 190 as shown in FIG. 9.

The flow restoration device 190 may then be retracted proximally towards the distal end 122 of the catheter 120, e.g., with the cutting head 142 and vacuum activated to facilitate pulling material 92 towards the distal end 122 and cutting head 142. The expandable member 192 may sufficiently engage the wall of the body lumen 90 to scrape or otherwise remove adherent material from the wall of the body lumen 90 and direct the material towards the distal 122 of the catheter 120.

Alternatively, the shaft 196 of the flow restoration device 190 may be coupled to an axial clutch device (not shown) within the handle 180 of the apparatus 110. In this alternative, the clutch device may be activated before, after, or when the motor 162 and/or vacuum source 160 are activated. During use, the clutch device is free to pass over the shaft 196 in a distal direction, e.g., during the outstroke of the cutting head 142, but engages the shaft 196 during the instroke of the cutting head 142, thereby directing the shaft 196 and expandable member 192 proximally within the body lumen 90. Thus, each stroke of the cutting head 142 may pull the expandable member 192 proximally a predetermined distance to automatically pull material 92 within the body lumen 90 towards the cutting head 142 and distal end 122 of the catheter 120. The location of the expandable member 192 may be set at a minimum distance from the distal end 122 of the catheter 120 before activation to ensure that a desired section of the body lumen 90 is scraped as the material 92 is macerated and aspirated by the apparatus 110.

Figure 10:
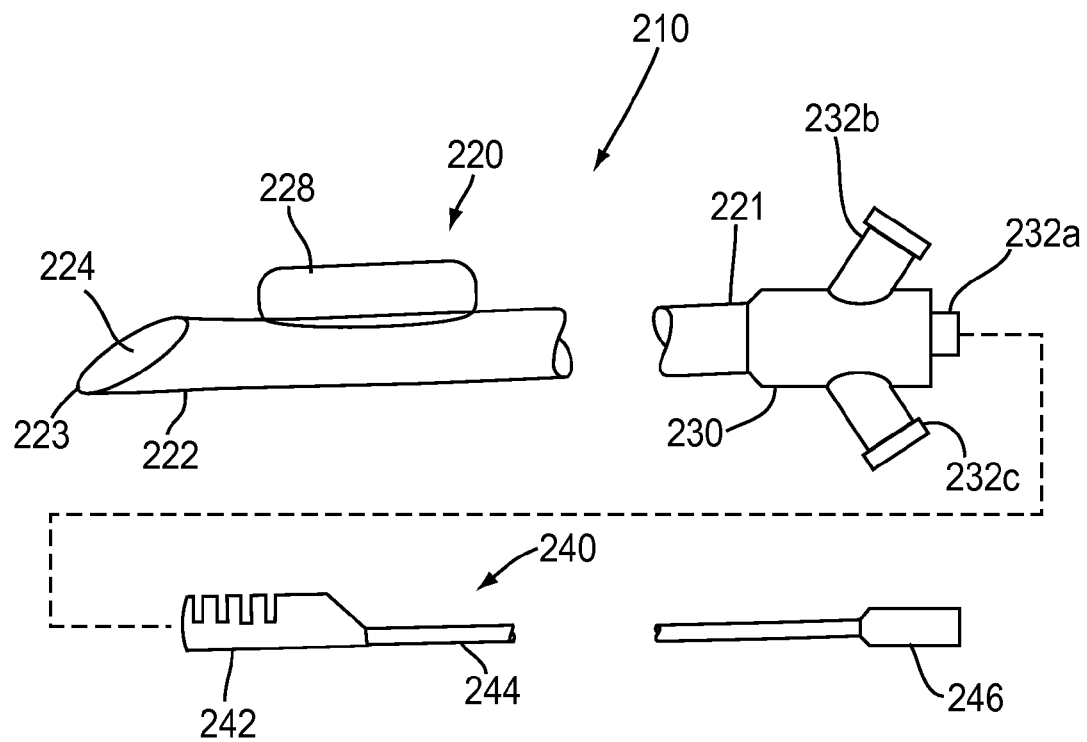
FIG. 10 is a side view of another exemplary system for capturing material from a body lumen including a sheath and a cutting assembly.
Figure 11:
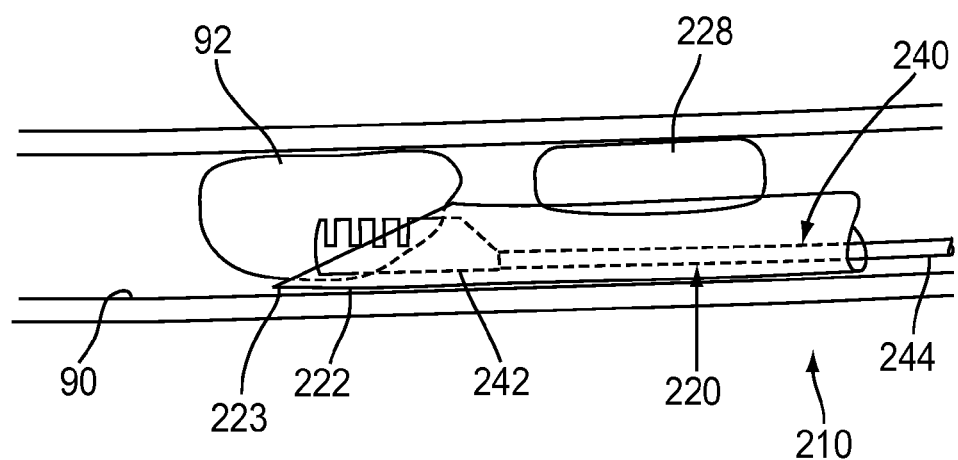
FIG. 11 is a cross-sectional view of a body lumen showing a method for removing material from a body lumen using the system of FIG. 10.

Turning to FIGS. 10 and 11, another embodiment of an apparatus 210 is shown that includes a catheter, sheath, or other tubular member 220 and a cutting assembly 240. Similar to the previous embodiments, the catheter 220 includes a proximal end 221, a distal end 222, and an aspiration lumen 224 extending therebetween. Unlike the previous embodiments, the catheter 220 includes a balloon or other expandable member 228 adjacent the distal end 222. For example, if the distal end 222 is beveled, the balloon 228 may be provided on an outer wall of the catheter 220 opposite the leading edge of beveled tip 223, as shown.

The balloon 228 may be formed from compliant or semi-compliant material, e.g., such that the balloon 228 conforms to surrounding anatomy when the balloon 228 is expanded. Thus, the balloon 228 may expand to substantially occlude a body lumen within which the catheter 220 is disposed, which may prevent escape of material past the catheter 220 during use, as described further below.

As shown, the balloon 228 may be bonded or otherwise attached on only one side of the distal end 222 of the catheter 220. Alternatively, a balloon may be provided that extends partially or entirely around the circumference of the distal end 222 of the catheter 220. In this alternative, the balloon may be biased or otherwise constructed to expand primarily or exclusively in one direction, e.g., radially outwardly opposite from the beveled tip 223.

Alternatively, the balloon 228 may be formed from noncompliant material, e.g., such that the balloon 228 expands to a predetermined shape, which may press the catheter 220 against the wall of the body lumen opposite the balloon 228 without necessarily sealing the body lumen. In a further alternative, other expandable members may be provided instead of the balloon 228. For example, an expandable mesh or frame (not shown) may be provided on the catheter 220, which may be expanded by activating an actuator on a handle 230 of the catheter 220. The mesh or frame may include a membrane such that, when the mesh or frame is expanded within a body lumen, the expandable member may be substantially nonporous to reduce migration of material past the catheter 220. Alternatively, the mesh or frame may be porous, if desired, e.g., to allow continued flow along the body lumen 90.

The cutting assembly 240 includes a cutting head 242 (which may be any of the embodiments described herein) and a shaft 244, which may also be generally similar to the previous embodiments. However, in this embodiment, the cutting assembly 240 is separate from the catheter 220 but may be selectively inserted into and/or removed from the catheter 220 during use.

A handle 230 is provided on the proximal end 221 of the catheter 220 that includes a plurality of ports 232. One or more of the ports 232 may include a hemostatic seal (not shown), a Luer or other connector (also not shown), and the like. For example, a first port 232a may include one or more hemostatic seals and a female Luer connector (not shown), which may accommodate receiving the cutting assembly 240 therein. For example, the cutting head 242 may be sufficiently small to be received through the first port 232a and into the aspiration lumen 224 of the catheter 220. The proximal end 246 of the cutting assembly 240 may include a male Luer or other connector that corresponds to a connector on the first port 232a. The catheter 220 and shaft 244 may have relative lengths such that, when the connectors are engaged, the cutting head 242 is disposed within the aspiration lumen 224 immediately adjacent the distal end 222, similar to the previous embodiments.

If the distal end 222 of the catheter 220 includes the beveled tip 223, the cutting assembly 240 and/or catheter 220 connectors may including features to ensure that the cutting assembly 240 is coupled to the catheter in a predetermined radial orientation, e.g., to ensure that the cutting head 242 is positioned radially within the distal end of the catheter 220 with the teeth 248 oriented away from the beveled tip 223. For example, the connectors on the first port 232a and the proximal end 246 of the cutting assembly 240 may including mating tabs and slots, or other features (not shown) that permit the cutting assembly 240 to be secured to the catheter 220 only in the predetermined orientation. Alternatively, the catheter 220 may include a channel or other track (not shown) within the aspiration lumen 224 that the cutting head 242 and/or shaft 244 may be advanced along within the aspiration lumen 224 to ensure that the cutting head 242 is maintained in the desired orientation relative to the beveled tip 223.

A second port 232b on the handle 230 may communicate with an interior of the balloon 228 via an inflation lumen (not shown) in the catheter 220. Thus, a source of inflation media (not shown) may be coupled to the port 232b and used to selectively expand and collapse the balloon 228. Finally, a third port 232c on the handle 230 may communicate with the aspiration lumen 224 and may allow a vacuum source to be coupled to the third port 232c for aspirating material from the distal end 222 of the catheter 220, similar to the previous embodiments.

Alternatively, an internal vacuum source may be provided within the handle 230, e.g., a syringe device (not shown), similar to that described above. In addition, the handle 230 may include a control system (also not shown) that may be coupled to the shaft 244 of the cutting assembly 240 when it is received through the handle 230 into the aspiration lumen 224.

Turning to FIG. 11, during use, the catheter 220 may be positioned within a body lumen 90 having material 92 therein that is to be removed. The catheter 220 may be introduced simply to remove the material 92. Alternatively, the catheter 220 may be placed in the body lumen 90 to perform a diagnostic and/or therapeutic procedure therein. For example, one or more instruments, e.g., guidewires, catheters, embolectomy devices, flow restoration devices, and the like (not shown), may be inserted into the first port 232a, through the aspiration lumen 224 and beyond the distal end 222 of the catheter 220 to perform a procedure within or beyond the body lumen 90. Once the procedure is complete, any instruments may be removed, and then the cutting assembly 240 may be inserted into the first port 232a and through the aspiration port 224 to position the cutting head adjacent the distal end 222. The cutting assembly 240 may be locked relative to the catheter 220 with the cutting head 242 within the distal end 222, e.g., using the mating connectors on the first port 232a and proximal end 246 of the cutting assembly 240, as described above.

After the catheter 220 is positioned to a desired location within the body lumen 90, the balloon 228 may be inflated to press against the wall of the body lumen 90, thereby pushing the catheter 220 against the opposite side of the body lumen 90. Thus, the beveled tip 223 of the distal end 222 may be pushed against or adjacent the wall of the body lumen 90. The cutting assembly 240 and/or vacuum source may then be activated to macerate and/or aspirate the material 92 into the catheter 220. As the cutting head 242 reciprocates relative to the distal end 222 of the catheter 220, the cutting head 242 may move between a proximal position fully within the aspiration lumen 242 and a distal position wherein the cutting head 242 does not extend beyond the beveled tip 223. This may reduce the risk of the cutting head 242 contacting the wall of the body lumen 90 and/or otherwise damaging the body lumen 90.

In addition, the balloon 228 may ensure that the teeth 248 of the cutting head 242 are oriented towards the center of the body lumen 90, thereby also reducing the risk of the teeth 248 or other features of the cutting head contacting the wall of the body lumen 90. In addition or alternatively, the balloon 228 may also press the distal end 222 against the body lumen 90 to reduce the risk of material 92 breaking free and escaping beyond the distal end 222 of the catheter 220.

After sufficient material 92 has been macerated and aspirated from the body lumen 90, the cutting head 242 may be turned off, the vacuum source deactivated, and the balloon 228 deflated. The cutting assembly 240 may be removed from the catheter 220 before the catheter 220 is removed, or alternatively, both the cutting assembly 240 and catheter 220 may be removed at the same time.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for removing material within a body lumen, comprising:

an elongate tubular member including a proximal end, a distal end sized for introduction into a body lumen, and an aspiration lumen extending between the proximal and distal ends and that is defined by an aspiration lumen wall, the distal end having a flexibility to facilitate advancement through tortuous anatomy;

a cutting head disposed within the aspiration lumen adjacent the distal end, the cutting head being reciprocable axially between distal and proximal positions within the aspiration lumen for macerating material being aspirated into the aspiration lumen, wherein the cutting head comprises a plurality of teeth and is capable of extending at least partially from the distal end of the elongate tubular member;

a drive shaft extending from the cutting head through the aspiration lumen to the proximal end of the tubular member;

a control system coupled to the cutting head that reciprocates the cutting head axially between the distal and proximal positions, wherein the control system includes a motor coupled to the drive shaft for reciprocating the drive shaft axially through the aspiration lumen, thereby reciprocating the cutting head axially within the aspiration lumen;

a flow restoration device deployable distally beyond the distal end of the tubular member, the flow restoration device comprising a shaft slidably received within the tubular member and an expandable member on a distal tip thereof that is expandable to a size larger than the distal end of the tubular member for engaging a wall of a body lumen to direct material within the body lumen towards the distal end of the tubular member when the flow restoration device is retracted proximally towards the distal end after deployment; and a clutch device that is free to pass over the shaft of the flow restoration device during an outstroke of the cutting head and engages the shaft of the flow restoration device during an instroke of the cutting head such that each stroke of the cutting head pulls the expandable member proximally a predetermined distance.

2. The apparatus of claim 1, further comprising a vacuum source communicating with the aspiration lumen for selectively applying vacuum to the aspiration lumen to aspirate material into the distal end of the tubular member.

3. The apparatus of claim 1, wherein the control system is carried within a handle on the proximal end of the tubular member.

4. The apparatus of claim 3, wherein the control system is configured for reciprocating the cutting head at speeds of about 3,600-60,000 cycles per minute.

5. The apparatus of claim 3, wherein the control system is configured for reciprocating the cutting head at speeds of about ten thousand cycles per minute or more.

6. The apparatus of claim 1, wherein the cutting head comprises a rounded, atraumatic distal tip that is exposed from the distal end of the tubular member and each tooth of the plurality of teeth extends proximally from the distal tip along a side edge of the cutting head.

7. The apparatus of claim 1, wherein the distal end of the tubular member terminates in a beveled tip having a leading edge on one side of the tubular member distal end, the tubular member further comprising an expandable member on only one side of an outer wall of the tubular member opposite the leading edge of the beveled tip.

8. The apparatus of claim 7, wherein the cutting head is reciprocable relative to the distal end of the tubular member such that the cutting head moves between the proximal position fully within the aspiration lumen and the distal position wherein the cutting head does not extend beyond the beveled tip.

9. The apparatus of claim 1, wherein the expandable member of the flow restoration device comprises one or more helical elements for moving adherent material from a wall of a body lumen within which the apparatus is disposed.

10. The apparatus of claim 1, wherein the cutting head comprises a cutting head distal tip and the plurality of teeth extend along a side edge of the cutting head, and wherein the cutting head is movable along one side of the aspiration lumen wall with the plurality of teeth oriented inwardly towards a center of the aspiration lumen.

11. The apparatus of claim 10 wherein the side edge extends proximally from the cutting head distal tip substantially parallel to a longitudinal axis of the apparatus.

12. The apparatus of claim 10 wherein the plurality of teeth are spaced apart axially from one another along the side edge.

13. The apparatus of claim 1, wherein the plurality of teeth extend along a side edge of the cutting head, and wherein the apparatus further comprises an expandable member on the distal end configured to expand outwardly from the distal end to reduce the risk of the plurality of teeth contacting the wall of the body lumen within which the distal end is introduced.

14. The apparatus of claim 1, wherein the tubular member comprises a guidewire lumen adjacent the aspiration lumen such that the apparatus may be advanced over a guidewire loaded into the guidewire lumen.

15. The apparatus of claim 1, wherein the tubular member comprises a shaft lumen for slidably receiving the shaft of the flow restoration device.

\* \* \* \* \*